US011275087B2

(12) United States Patent
Gouda et al.

(10) Patent No.: US 11,275,087 B2
(45) Date of Patent: Mar. 15, 2022

(54) TEST SUPPORT METHOD FOR SUPPORTING PREDICTION OF PATHOLOGICAL COMPLETE RESPONSE (PCR) USING FLUORESCENT NANOPARTICLES

(71) Applicant: Konica Minolta, Inc., Tokyo (JP)

(72) Inventors: Hideki Gouda, Tokyo (JP); Masaru Takahashi, Kokubunji (JP); Kensaku Takanashi, Hino (JP); Hisatake Okada, Tachikawa (JP); Yuichi Ozaki, Hino (JP); Yuka Yoshihara, Hino (JP); Yasushi Nakano, Hino (JP); Kohsuke Gonda, Sendai (JP); Noriaki Ohuchi, Sendai (JP); Mika Watanabe, Sendai (JP); Norikazu Masuda, Toyonaka (JP); Masakazu Toi, Toyonaka (JP); Hiroshi Tada, Sendai (JP); Minoru Miyashita, Sendai (JP)

(73) Assignee: KONICA MINOLTA, INC., Tokyo (JP)

( * ) Notice: Subject to any disclaimer, the term of this patent is extended or adjusted under 35 U.S.C. 154(b) by 228 days.

(21) Appl. No.: 15/806,970

(22) Filed: Nov. 8, 2017

(65) Prior Publication Data
US 2018/0136212 A1   May 17, 2018

(30) Foreign Application Priority Data

Nov. 11, 2016 (JP) .............................. JP2016-220490
Jun. 5, 2017 (JP) .............................. JP2017-111031

(51) Int. Cl.
| | |
|---|---|
| *G01N 33/574* | (2006.01) |
| *G01N 33/52* | (2006.01) |
| *G01N 33/53* | (2006.01) |
| *G06K 9/00* | (2022.01) |
| *G01N 33/58* | (2006.01) |
| *G01N 1/30* | (2006.01) |
| *G01N 33/50* | (2006.01) |

(52) U.S. Cl.
CPC ......... *G01N 33/57415* (2013.01); *G01N 1/30* (2013.01); *G01N 33/5023* (2013.01); *G01N 33/582* (2013.01); *G06K 9/0014* (2013.01); *G06K 9/00134* (2013.01); *G06K 9/00147* (2013.01); *G01N 2333/71* (2013.01)

(58) Field of Classification Search
CPC ........... G01N 33/57415; G01N 33/582; G01N 2333/71; G01N 33/5023; G06K 9/00134; G06K 9/0014

See application file for complete search history.

(56) References Cited

U.S. PATENT DOCUMENTS

| | | | |
|---|---|---|---|
| 2010/0008975 A1* | 1/2010 | Amler | B65B 61/20 424/450 |
| 2013/0157895 A1* | 6/2013 | Aimiya | G01N 1/30 506/9 |
| 2013/0230866 A1* | 9/2013 | Miyashita | G01N 21/6428 435/7.23 |
| 2016/0371834 A1* | 12/2016 | Watanabe | G06K 9/00147 |

FOREIGN PATENT DOCUMENTS

| | | |
|---|---|---|
| WO | 2012029342 A1 | 3/2012 |
| WO | 2013146741 A1 | 10/2013 |
| WO | WO-2015002082 A1 * | 1/2015 ......... G06K 9/00147 |

OTHER PUBLICATIONS

Diermeier et al., Epidermal growth factor receptor coexpression modulates susceptibility to Herceptin in HER2/neu overexpressing breast cancer cells via specific erbB-receptor interaction and activation, Experimental Cell Research, 304:604-619. (Year: 2005).*
Extended European Search Report dated Feb. 22, 2018 from the corresponding European Application No. 17200777.5.
Kan Yonemori, et al:"Immunohistochemica expression of HER1, HER3, and HER4 in HER2-positive breast cancer patients treated with trastuzumab-containing neoadjuvant chemotherapy", Journal of Surgical Oncology, Jan. 1, 2010, pp. n/a-n/a.
Li Zhou, et al:"Quantum Dot-based Immunohistochemistry for Pathological Applications", Cancer Translational Medicine, vol. 2, No. 1, Jan. 1, 2016, pp. 21-28.
Minoru Miyashita, et al:"Quantitative diagnosis of HER2 protein expressing breast cancer by single-particle quantum dot imaging", Cancer Medicine, vol. 5, No. 10, Sep. 26, 2016, pp. 2813-2824.
Kohsuke Gonda, et al:"Predictive diagnosis of the risk of breast cancer recurrence after surgery by single-particle quantum dot imaging", Scientific Reports, vol. 5, No. 1, Sep. 22, 2015.

* cited by examiner

*Primary Examiner* — Hong Sang
(74) *Attorney, Agent, or Firm* — Lucas & Mercanti, LLP

(57) ABSTRACT

The present invention relates to a test support method which is a means for predicting whether or not pathological complete response (pCR) will be attained when a preoperative chemotherapy with an anticancer drug is performed, the method using a sample (breast cancer tissue section) collected from a breast cancer patient to be subjected to the preoperative chemotherapy. The test support method includes: [1] the step of acquiring a fluorescence image of a breast cancer tissue section, which fluorescence image shows bright spots of fluorescent nanoparticles labeling one or more kinds of breast cancer-related proteins; [2] the step of acquiring at least one index relating to the expression level(s) of the breast cancer-related protein(s) on the basis of the bright spots of the fluorescence image; and [3] the step of acquiring information for predicting pCR by performing an analysis using the above-described at least one index.

7 Claims, 26 Drawing Sheets

[Fig. 1]
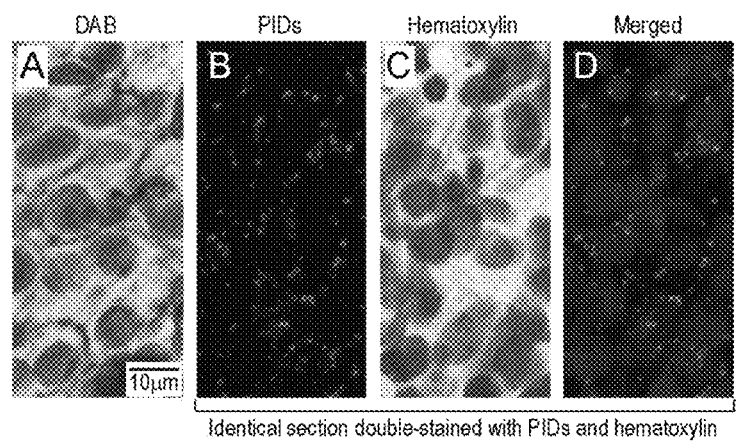
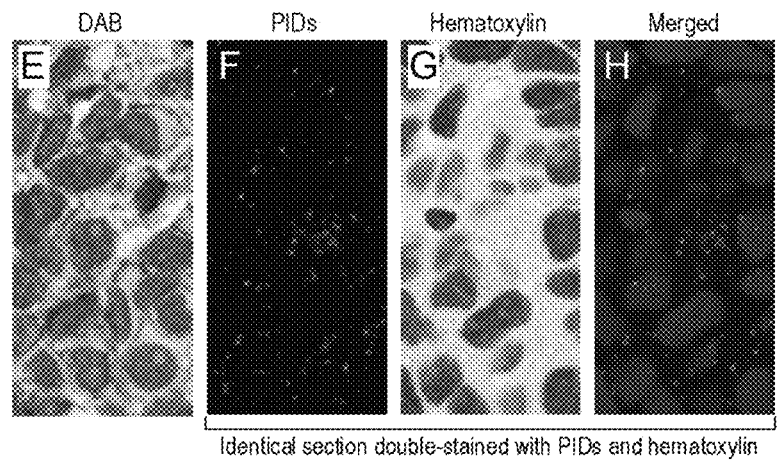

[Fig. 2]
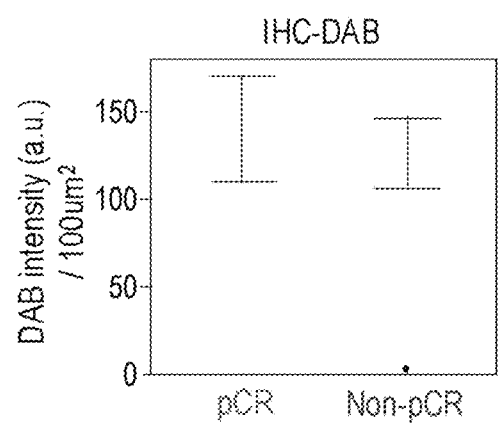

[Fig. 3]
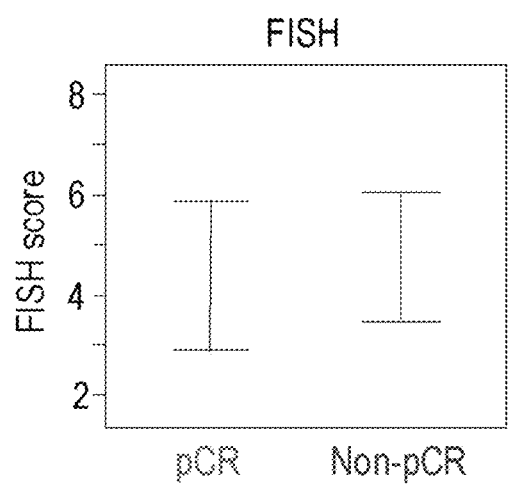

[Fig.4]
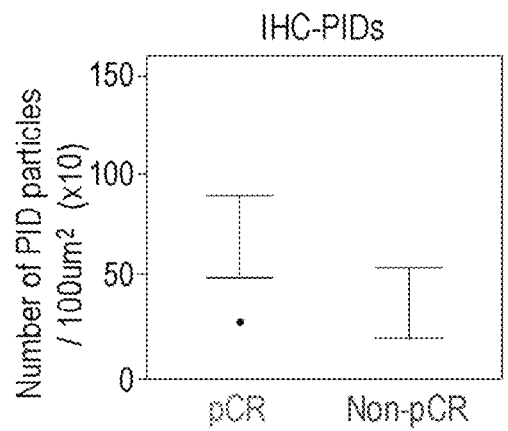

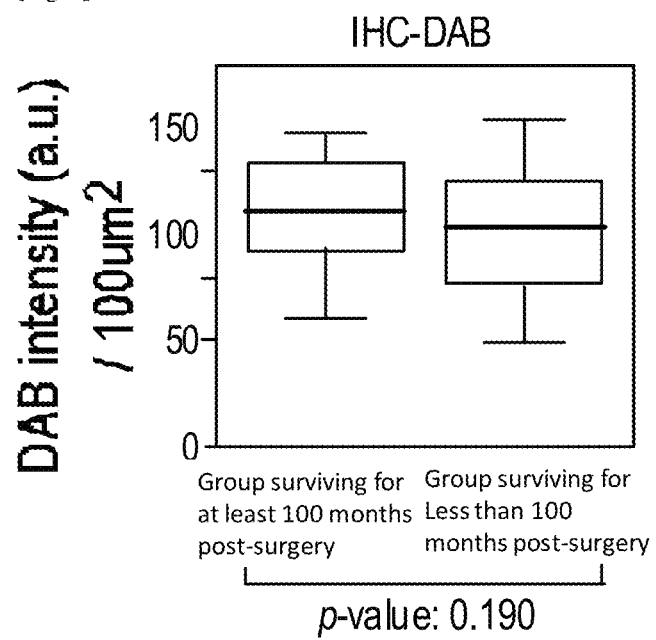
[Fig. 5]

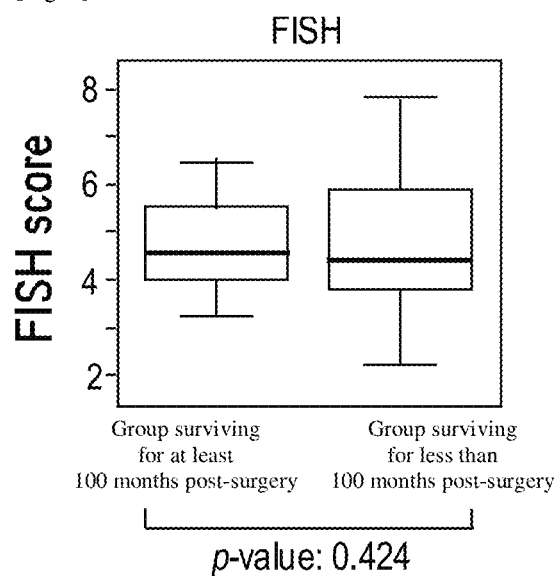
[Fig. 6]

[Fig. 7]
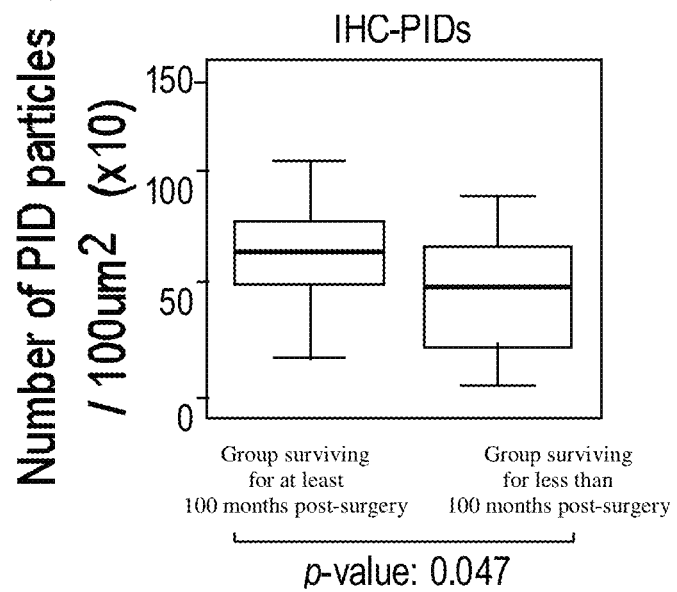

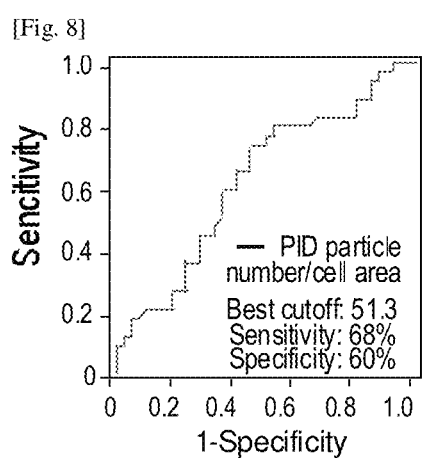
[Fig. 8]

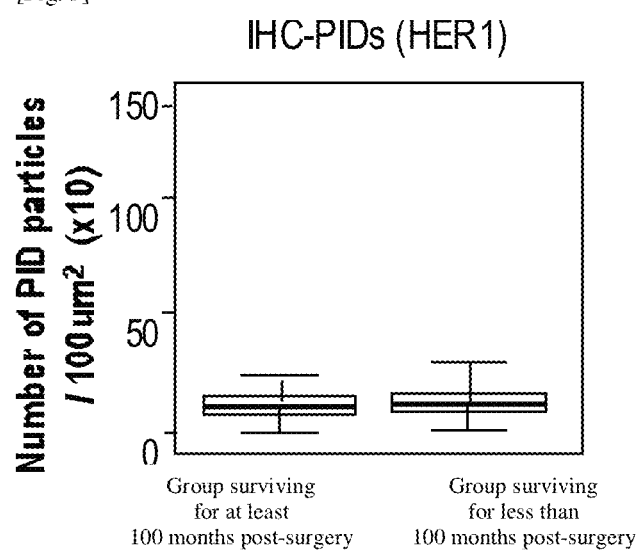
[Fig. 9]

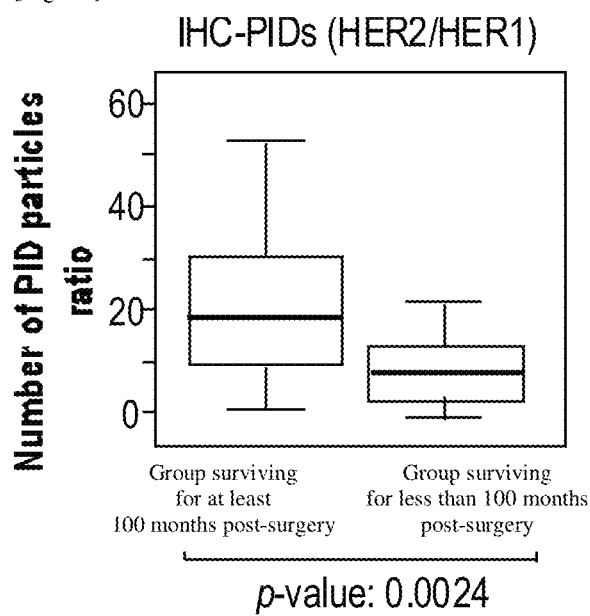
[Fig. 10]

[Fig. 11]
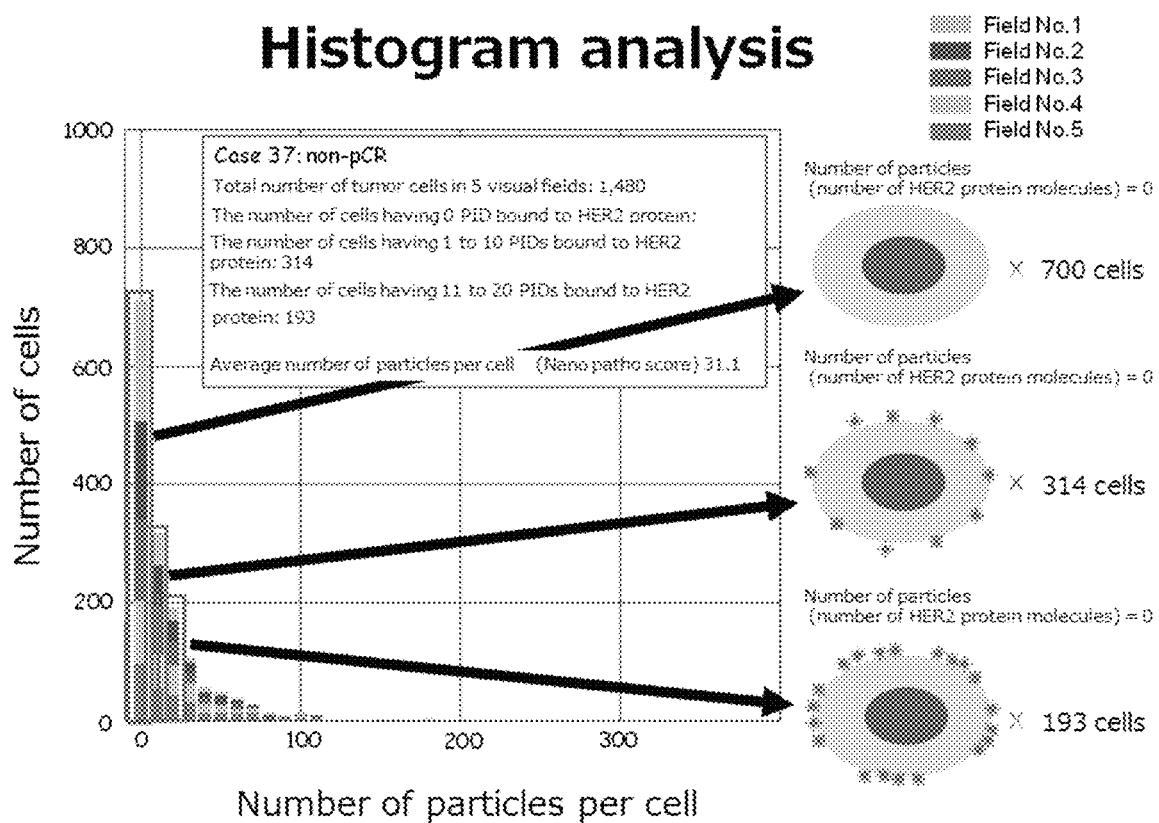

[Fig. 12-1]
No.3-27 (pCR)
Therapy: FEC-HER+DTX
(A) Pattern having a peak at the number of bright spots = 0
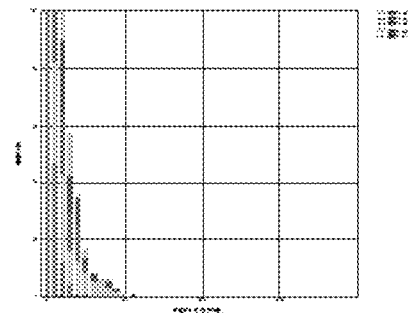
No.3-28 (pCR)
Therapy: FEC-HER+DTX
(C) Bimodal or multimodal pattern
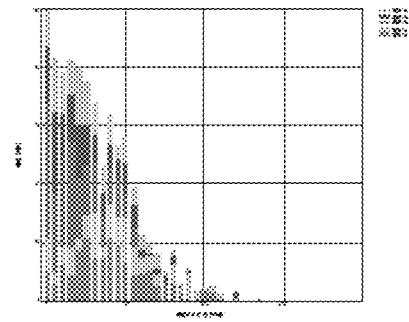
No.3-29 (pCR)
Therapy: FEC-HER+DTX
(D) Pattern distributed over a wide range of classes
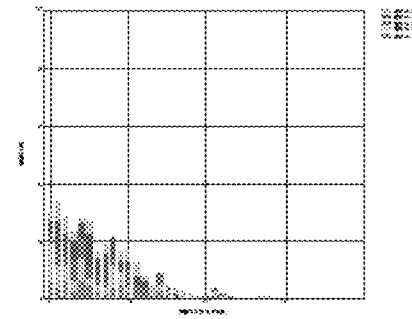
No.3-30 (pCR)
Therapy: FEC-HER+DTX
(B) Unimodal pattern in which the peak is shifted to the right
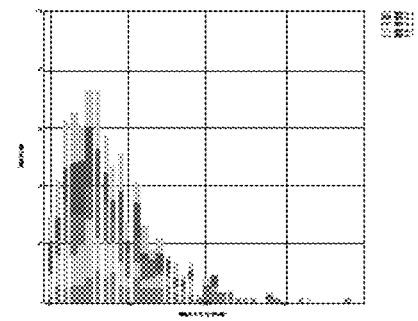

[Fig. 12-2]
No.3-31 (pCR)
Therapy: EC-HER+DTX
(B) Unimodal pattern in which the peak is
    shifted to the right
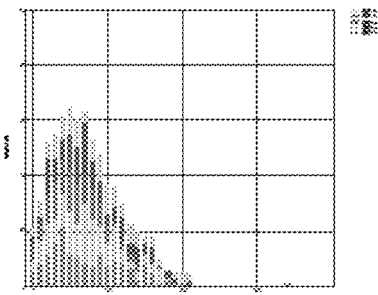
No.3-32 (pCR)
Therapy: FEC-HER+DTX
(B) Unimodal pattern in which the peak is
    shifted to the right
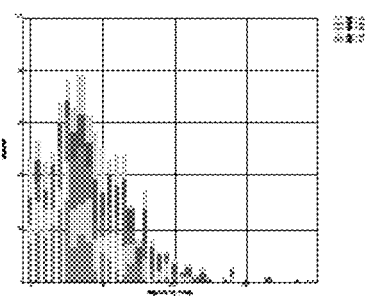
No.3-65 (non-pCR)
Therapy: FEC-HER+DTX
(A) Pattern having a peak
    at the number of bright spots = 0
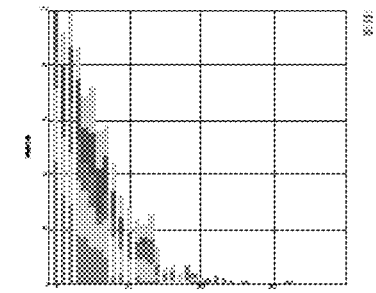
No.3-66 (non-pCR)
Therapy: FEC-HER+DTX
(A) Pattern having a peak
    at the number of bright spots = 0
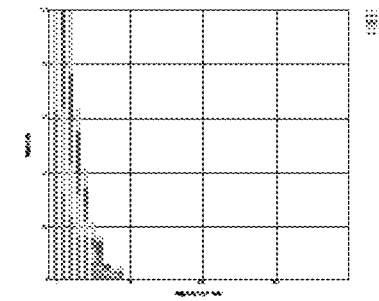

[Fig. 13]
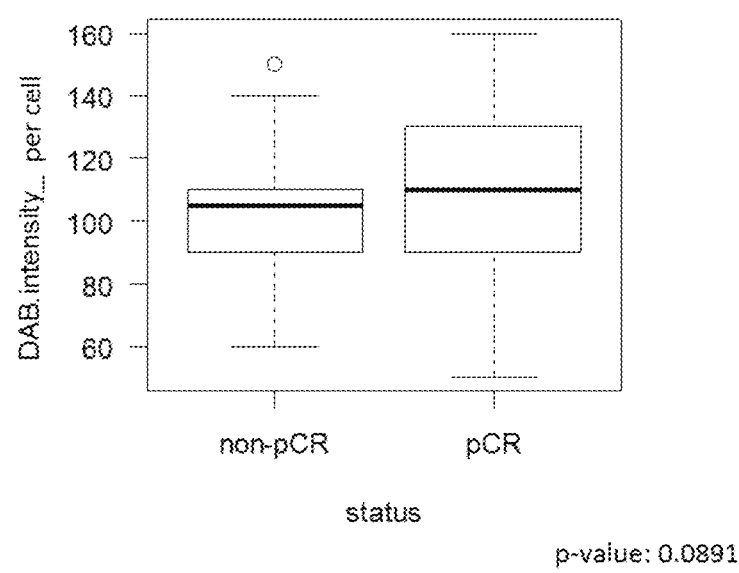

[Fig. 14]
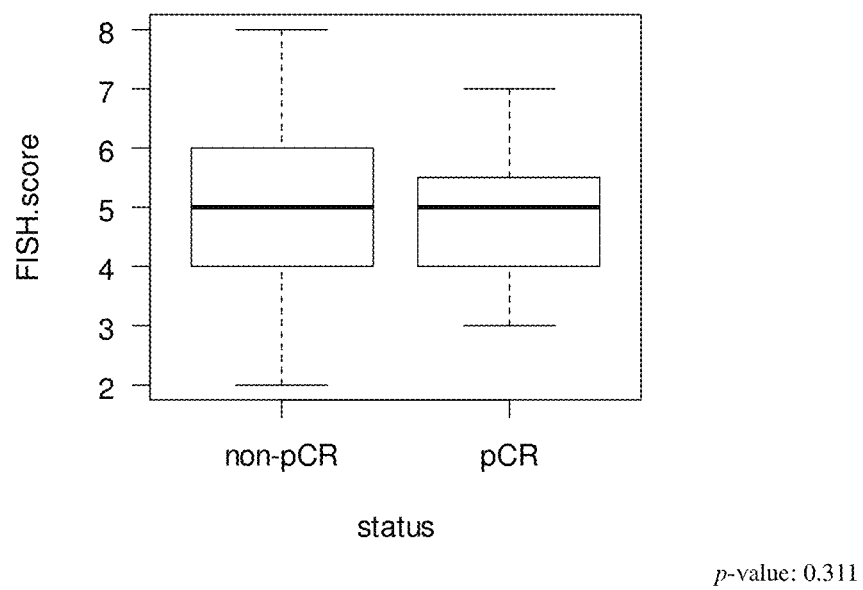
p-value: 0.311

[Fig. 15]
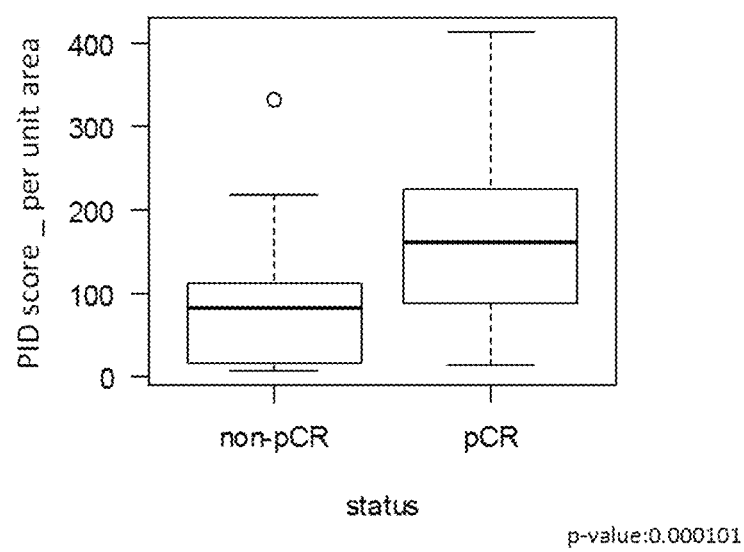

[Fig. 16]
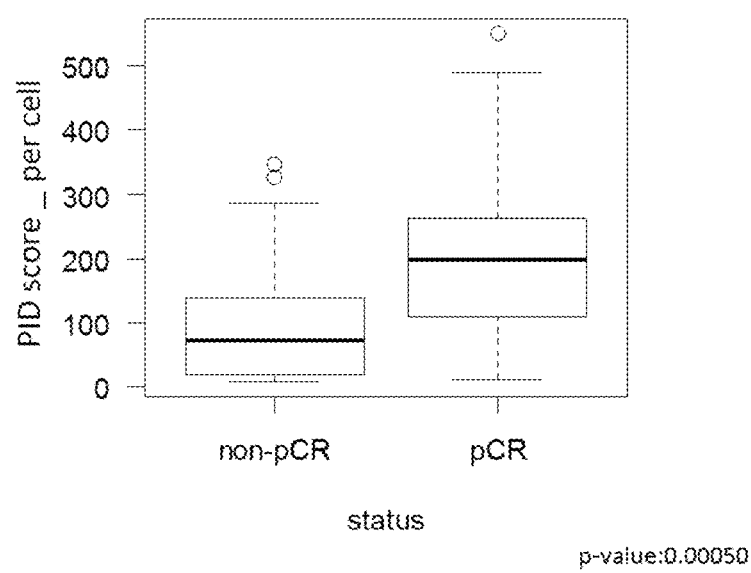

[Fig. 17]
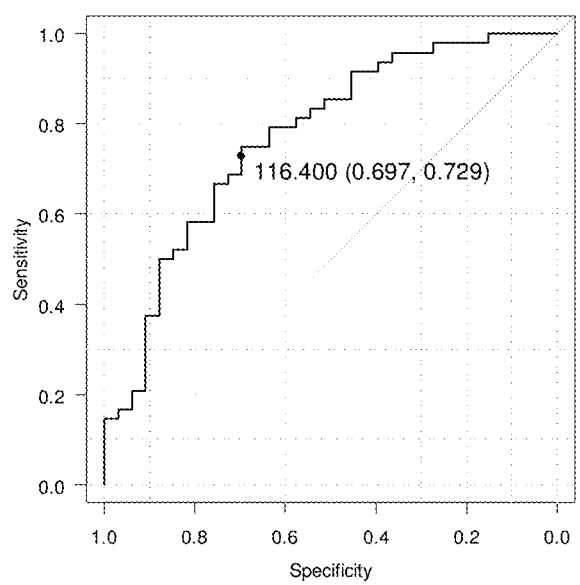

[Fig. 18]
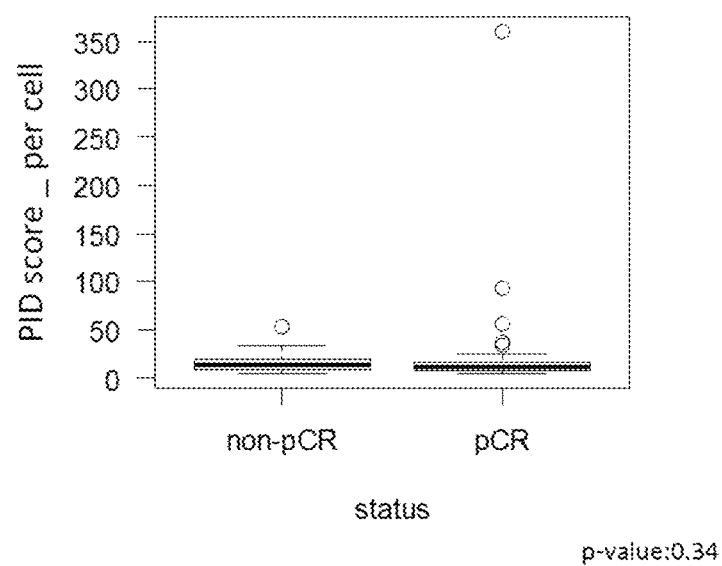

[Fig. 19]
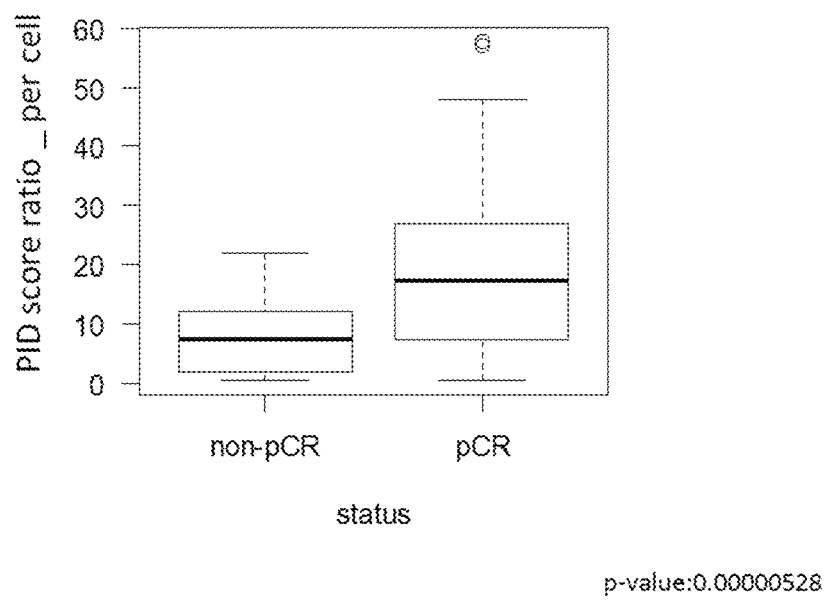
p-value:0.00000528

[Fig. 20]
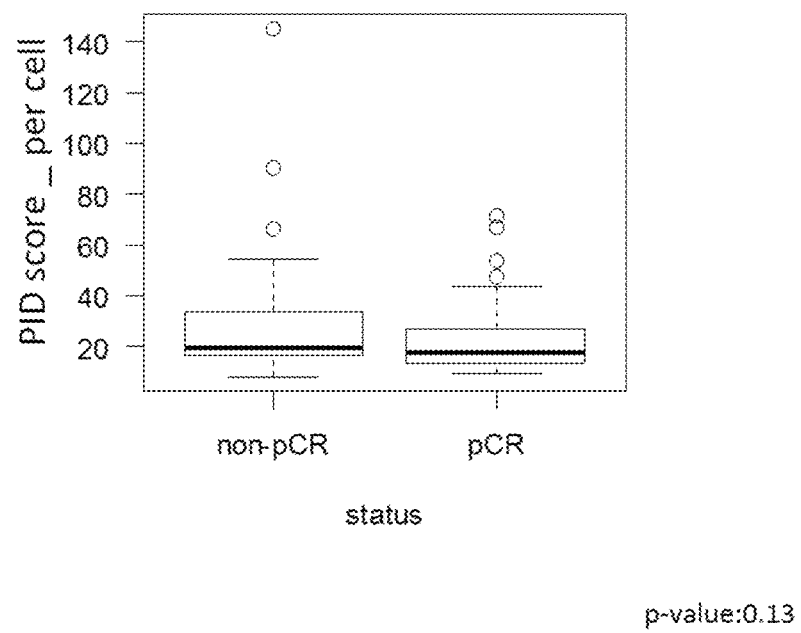

[Fig. 21]
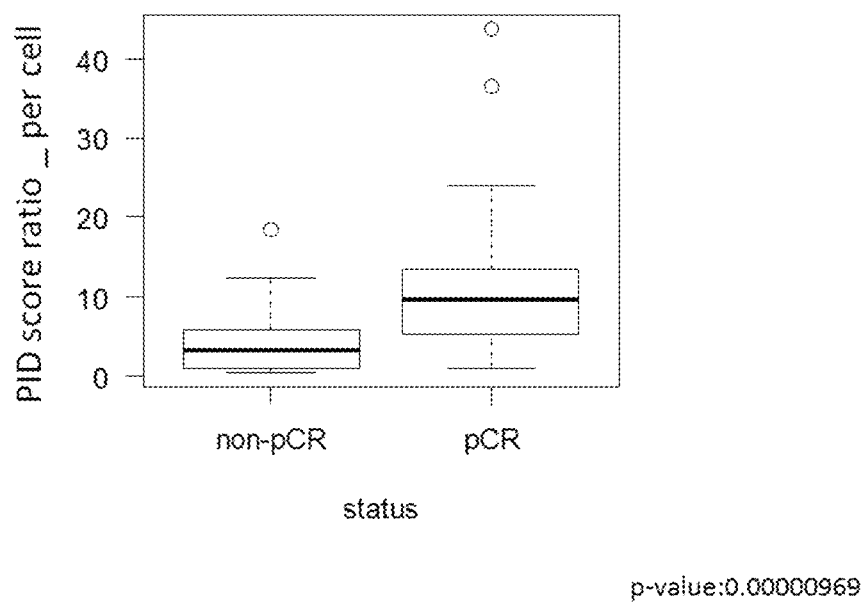
p-value:0.00000969

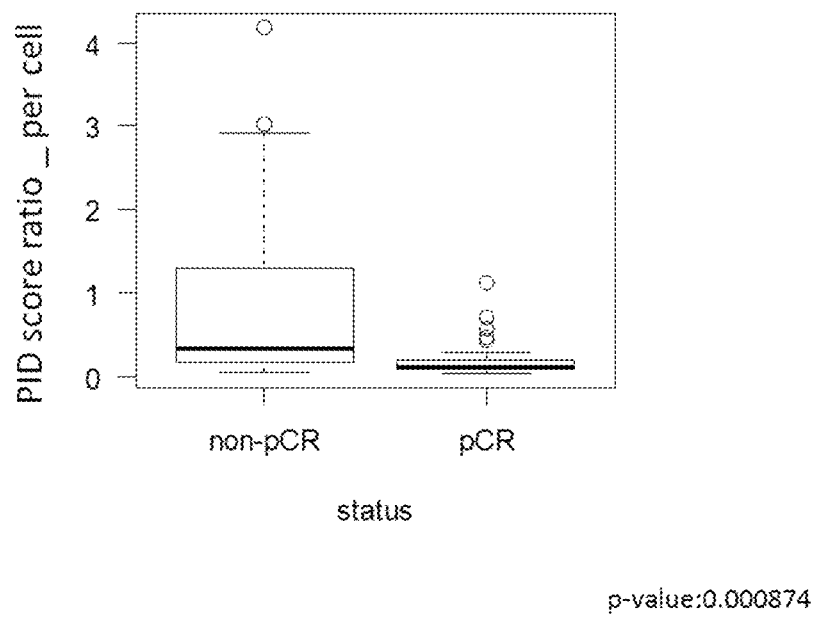
[Fig. 22]

[Fig. 23]
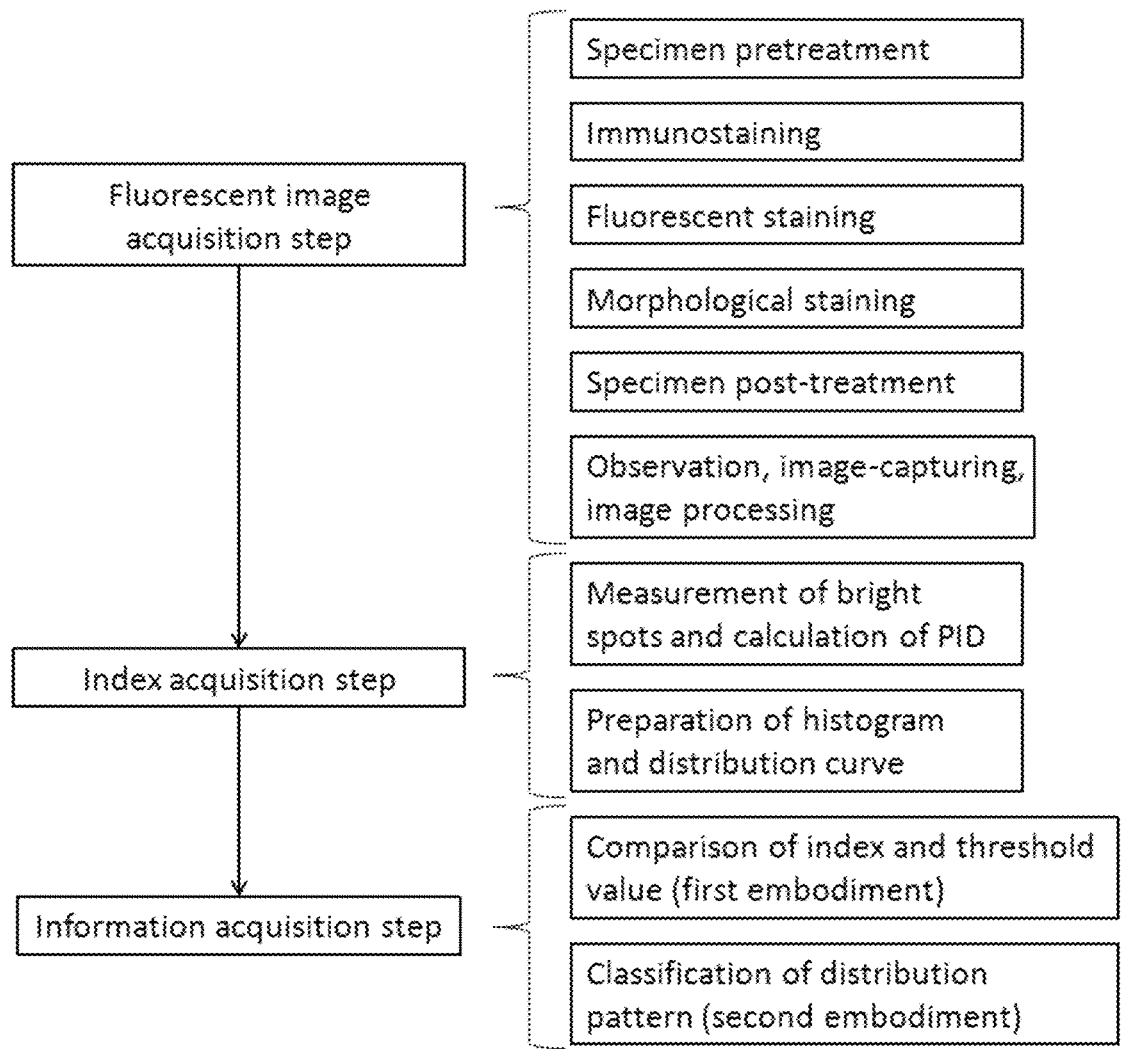

[Fig. 24]
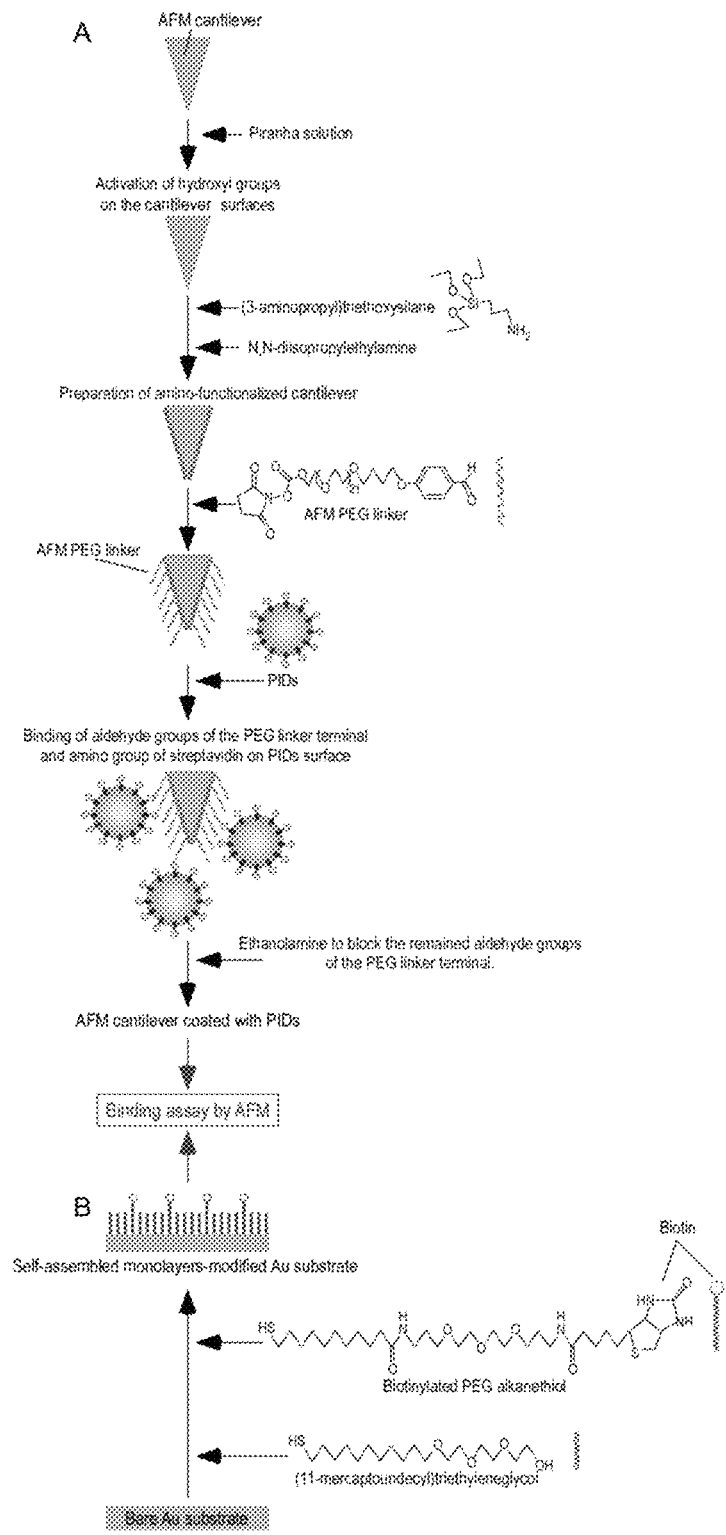

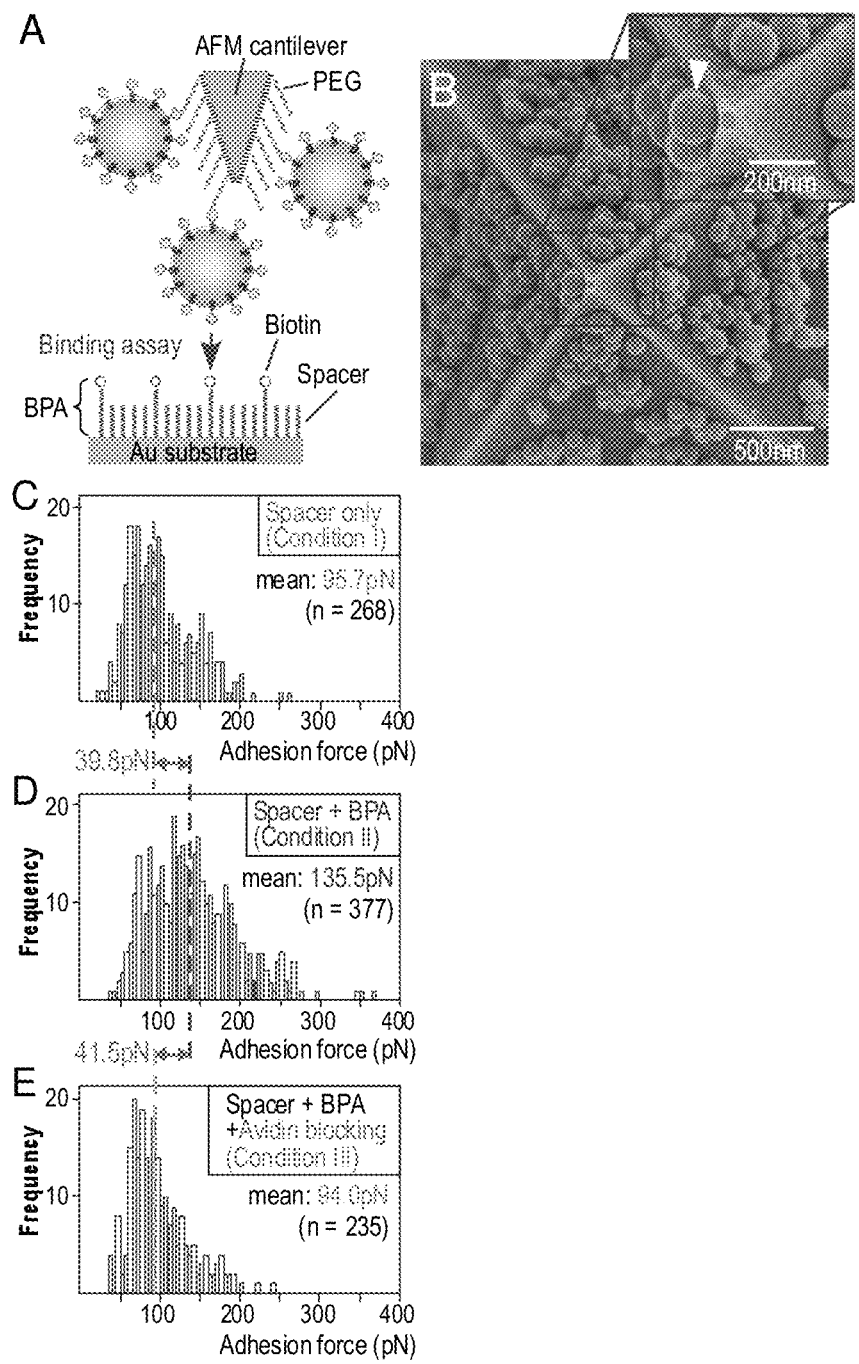
[Fig. 25]

US 11,275,087 B2

TEST SUPPORT METHOD FOR SUPPORTING PREDICTION OF PATHOLOGICAL COMPLETE RESPONSE (PCR) USING FLUORESCENT NANOPARTICLES

TECHNOLOGICAL FIELD

The present invention relates to a test support method for supporting the prediction of pathological complete response (pCR) to preoperative therapy in breast cancer by using a sample prepared from a breast cancer tissue collected from a breast cancer patient to be subjected to preoperative chemotherapy. More particularly, the present invention relates to a test support method which comprises: fluorescently labeling a breast cancer-related protein on a tissue section with fluorescent nanoparticles; and acquiring information for predicting pCR by performing an analysis using an index relating to the expression level of the breast cancer-related protein, which index is obtained from a fluorescence image of the thus labeled breast cancer-related protein.

BACKGROUND

A treatment with an anticancer drug that precedes a breast cancer surgery is referred to as "preoperative chemotherapy" or "neoadjuvant therapy". In the heyday of mastectomy in 1970s, preoperative chemotherapy used to be performed mainly for the purpose of increasing the effects of a surgery on a patient whose cancer had spread to the surrounding tissues and lymph nodes and was thus difficult to completely remove by a surgery alone (locally advanced breast cancer). It was considered that some of the patients who received such preoperative chemotherapy showed an effect thereof; however, the effect was not necessarily evaluated in a positive way, and it has been believed that, as compared to chemotherapy performed after a surgery, preoperative chemotherapy does not lead to "an improvement of prognosis (survival rate)", which is the primary object of a treatment. However, recent development of excellent anticancer drugs and hormone therapeutic drugs enabled to attain improved therapeutic effects by employing such drugs in combination with a surgery. Therefore, it has been advocated to call preoperative chemotherapy "PST (primary systemic treatment)" in the meaning of using preoperative chemotherapy on equal terms with a surgery.

A state where complete disappearance of cancer cells as a result of preoperative chemotherapy has been confirmed by a histopathological method using a microscope is referred to as "pathological complete response (pCR)", and it is an index with which an anticancer drug can be judged to be effective.

A molecular target drug "trastuzumab" (trade name "Herceptin" (registered trademark); an anti-HER2 monoclonal antibody), which specifically targets the HER2 protein expressed on the cell surface, is an anticancer drug that has been confirmed to have a certain efficacy/effect against "metastatic breast cancer observed with HER2 overexpression" in "postoperative auxiliary chemotherapy for breast cancer observed with HER2 overexpression". The HER2 protein is believed to perform signal transduction by forming a homodimer or a heterodimer bound with activated EGFR (HER1), HER3, or HER4, and it is presumed that the HER2 protein functions as the role of growth factor receptor in cancer cell (no endogenous ligand binding to HER2 has not been known). Amplification of the HER2 gene and overexpression of the HER2 protein are observed in 15 to 25% of a case of human breast cancer and, for example, it has been reported that breast cancer patients with HER2 gene amplification/HER2 protein overexpression have poor prognosis and show high sensitivity to anthracycline-based anticancer drugs (e.g., doxorubicin), and that such breast cancer patients show resistance to hormone therapy (e.g., tamoxifen) and CMF therapy (the use of a combination of cyclophosphamide, methotrexate and fluorouracil). From the standpoints of improvement of the cure rate and the medical economics, tests and evaluations of the HER2 gene (HER2/neu, c-erbB-2) amplification and HER2 protein overexpression are performed for selecting the subject cases of Herceptin and, for the management of the accuracy thereof, the ASCO/CAP HER2 Testing Guidelines was established in 2007 and revised in 2013.

In Japan as well, HER2 protein overexpression is evaluated by an immunohistochemical (IHC) method and HER2 gene amplification is evaluated by an in situ hybridization (ISH) method in accordance with the revised ASCO/CAP HER2 Testing Guidelines (HER2 Testing Guidelines 4th edition, Breast Cancer HER2 Testing and Pathology Committee, April 2014). In these evaluations, a formalin-fixed paraffin-embedded tissue block (sample) is prepared from a tissue of primary focus or metastatic focus of breast cancer, and a thin section thereof which is placed on a slide and stained by prescribed procedures is utilized. In the IHC method, the stainability and staining intensity of the membranes of cancer cells in a tissue section are indicated with a score on a four-point scale based on prescribed criteria (staining pattern): 3+ (positive: intense and complete staining of the entire membrane circumference is observed in >10% of cancer cells); 2+ (equivocal: incomplete and/or weak or moderate staining of the entire membrane circumference is observed in >10% of cancer cells, or intense and complete staining of the entire membrane circumference is observed in ≤10% of cancer cells); 1+ (negative: slight or barely partial staining of membranes is observed in >10% of cancer cells); or 0 (negative: no stained image is obtained, or incomplete and slight or barely partial staining of membranes is observed in ≤10% of cancer cells). In the ISH method, based on the ratio between the number of signals of the HER2 gene on a chromosome contained in the cancer cells of a tissue section and the number of signals of the CEP17 gene as a control (HER2/CEP17 ratio) as well as the average copy number of the HER2 gene per cell (HER2 gene average copy number), an evaluation of "positive" (HER2/CEP17 ratio≥2.0, or HER2/CEP17 ratio<2.0 and HER2 gene average copy number≥6.0), "equivocal" (HER2/CEP17 ratio<2.0 and HER2 gene average copy number≥4.0 to ≤6.0), or "negative" (HER2/CEP17 ratio<2.0 and HER2 gene average copy number<4.0) is given. The HER2 gene average copy number is customarily referred to as "ISH score". In cases where the ISH method is performed first, a treatment with trastuzumab is judged to be suitable when the evaluation result is positive and, even if the result is equivocal, a treatment with trastuzumab is nevertheless judged to be suitable as long as the result of the IHC method performed on the same sample is positive, or the result of the IHC method or ISH method performed on a different sample is positive. In cases where the IHC method is performed first, a treatment with trastuzumab is judged to be suitable when the evaluation result is positive (3+) and, even if the result is equivocal (2+), a treatment with trastuzumab is nevertheless judged to be suitable as long as the result of the ISH method performed on the same sample is positive, or the result of the IHC method or ISH method performed on a different sample is positive.

As the IHC method, conventionally, a DAB staining method (IHC-DAB method) in which an anti-HER2 antibody labeled with an enzyme (peroxidase) is bound to the HER2 protein contained in a tissue section of a tissue slide by a direct or indirect method and a substrate (diaminobenzidine) is subsequently allowed to react the resultant for color development has been generally employed. In such staining with an enzyme as in DAB staining, however, since the staining concentration is greatly affected by environmental conditions such as temperature and time, there is a problem that it is difficult to accurately estimate the actual amount of an antigen or the like based on the staining concentration.

Therefore, in recent years, as an alternative to a method of evaluating the expression level of a protein of interest (e.g., HER2) using a dye (one produced from a substrate by an enzyme) as in the IHC-DAB method, a method (IHC-PID method) of evaluating the expression level of a protein of interest using nano-size fluorescent particles, for example, particles in which a phosphor such as a fluorescent dye or quantum dot is integrated into a matrix such as a resin (phosphor-integrated particles or phosphor-integrated dots: PIDs), has been proposed and increasingly put into practice. When a protein of interest is labeled with phosphor-integrated particles and an excitation light suitable for the phosphor is irradiated thereto, the phosphor-integrated particles can be observed as high-luminance bright spots that indicate the number and positions of the protein of interest with high accuracy, and the bright spots can be observed and photographed over a long period of time since their color is unlikely to fade. For instance, WO 2012/029342 (Patent Document 1), WO 2013/146741 (Patent Document 2) and the like describe IHC-PID methods where a protein of interest is immunostained with phosphor-integrated particles (also referred to as "fluorescent aggregates", "fluorescent substance-integrated particles" or the like).

The above-mentioned Patent Documents each relate to a method of quantifying a breast cancer-related protein (e.g., HER2) or a breast cancer-related gene using phosphor-integrated particles. However, these Patent Documents and other patent documents and non-patent documents do not offer any description with regard to the point that such a quantification method enables to predict whether or not pathological complete response (pCR) is attained when a preoperative chemotherapy is performed using an anticancer drug, or matters that relate to a test support method based on the prediction.

RELATED ART REFERENCES

Patent Documents

[Patent Document 1] WO 2012/029342
[Patent Document 2] WO 2013/146741

SUMMARY

To achieve at least one of the abovementioned objects, according to an aspect of the present invention, a test support method which is a means for predicting whether or not pathological complete response (pCR) will be attained when a preoperative chemotherapy with an anticancer drug is performed, the method using a breast cancer tissue section prepared from a breast cancer patient to be subjected to the preoperative chemotherapy.

For the completion of the present invention, the present inventors used samples collected at Tohoku University Hospital during the period of 2007 to 2014, or samples collected for JBCRG-16 (Neo-LaTH test) by JBCRG (Japan Breast Cancer Research Group) in 2016. All of these samples were permitted for use by the Tohoku University School of Medicine Ethics Committee and JBCRG. That is, for the completion of the present invention, samples collected prior to a preoperative chemotherapy from plural breast cancer patients who eventually exhibited pCR (pCR group) and samples collected prior to a preoperative chemotherapy from plural breast cancer patients who did not exhibit pCR eventually (non-pCR group) were used, and the expression level of HER2 contained in each sample was quantified by an IHC-PID method, an IHC-DAB method and a FISH method, the results of which were compared between the pCR group and the non-pCR group. In addition, the expression levels of breast cancer-related proteins other than HER2, such as HER1 and HER3, were also quantified by an IHC-PID method, an IHC-DAB method and a FISH method in the same manner, and the results thereof were compared between the pCR group and the non-pCR group. Moreover, in the IHC-PID method, histograms were prepared from the quantification results of the HER2 expression level, and their distribution patterns were compared between the pCR group and the non-pCR group.

As for the HER2 expression level, in the quantification results obtained by the IHC-DAB method (a case where the color intensity of DAB measured by an apparatus, not the four-point-scale score according to the HER2 Testing Guidelines, was used as an index) and the quantification results obtained by the FISH method (a case where the above-described HER2 gene average copy number (FISH score) was used as an index), no statistically significant difference was found between the pCR group and the non-pCR group (FIGS. 13 and 14). There has not been any report on a case where such a significant difference was found using an IHC-DAB method or a FISH method, and the findings of no significant difference are recognized as reconfirmation of a well-known fact.

On the other hand, in the quantification results obtained by the IHC-PID method, for both cases where the number of PID particles per unit tissue area was used as an index of the expression level (PID score) and where the average number of PID particles per cell was used as an index of the expression level (PID score), a statistically significant difference was found between the pCR group and the non-pCR group (FIGS. 15 and 16). Further, a statistically significant difference was also found when the HER2 expression level and the HER1 or HER3 expression level, which were quantified by the IHC-PID method, were combined and, for example, the ratio of the HER2 expression level with respect to the HER1 expression level (HER2 expression level/HER1 expression level) or the ratio of the HER2 expression level with respect to the HER3 expression level (HER2 expression level/HER3 expression level) was calculated and the value thereof was compared between the pCR group and the non-pCR group (FIGS. 21 and 22). Moreover, the distribution pattern of the histogram representing the HER2 expression level quantified by the IHC-PID method was also found to show different trends between the pCR group and the non-pCR group. It is noted here that, since an evaluation of the expression level by the IHC-DAB method according to the HER2 Testing Guidelines only yields a non-quantitative score on a four-point scale (3+, 2+, 1+ or 0) as described above and the FISH method also provides nothing more than similar multi-grade evaluations (whether the HER2/CEP2 ratio is 2.0 or higher or lower than 2.0, and whether the HER2 average copy number is 6.0 or greater, 4.0 to less than 6.0, or less than 4.0), even though a histogram can be prepared based on such evaluation results, it is not possible to find a characteristic feature in the distribution pattern thereof due to insufficient number of classes. Furthermore, even though a histogram can be prepared based on such quantitative evaluations using the color intensity of the IHC-DAB method as an index, no clear difference in trend can be found between the pCR group and the non-pCR group.

A conventional FISH method (whose subject is a gene) and the IHC-PID method of the present invention (whose subject is a protein) are similar in that the former measures the number of signals provided by a fluorescent dye and the latter measures the number of bright spots, namely fluorescent nanoparticles. However, in the FISH method, a large signal is often generated due to aggregation of plural fluorescent dye molecules (cluster formation) and in such a case, for convenient evaluation in the measurement of the number of signals, a rule of, for example, assigning a FISH score of 5 to large signals and assigning a FISH score of 3 to moderate signals, is implemented. Under such a rule, it is hard to say that the number of the HER2 genes is accurately measured and, in principle as well, an accurate measurement cannot be achieved. It is therefore believed that a clear difference in trend could not be drawn between the pCR group and the non-pCR group because of the inaccuracy of the values of the HER2 gene average copy number quantified by the FISH method.

On the other hand, in the present invention, since the number of HER2 protein molecules is accurately obtained in accordance with the below-described principle, the number of bright spots (PID score) in a histogram is believed to have an accuracy of two-digits or more. Accordingly, it is also believed that an effect of predicting whether or not pCR will be attained, which could not be discovered based on the quantification using the color intensity of IHC-DAB method or the fluorescence intensity of FISH method as an index, was obtained. Moreover, in the future, it is expected to be also possible to predict pCR through preparation of a histogram, classification of its distribution pattern and the like based on the results of performing a HER2 gene quantification method using fluorescent nanoparticles (ISH-PID method) as a modified FISH method.

The quantification principle of the present invention can be summarized in that a single breast cancer-related protein (e.g., HER2) contained in a patient tissue is marked with a single fluorescent nanoparticle. The detection of HER2 by the IHC-DAB method or FISH method utilizes amplification reaction, that is, plural dye molecules are generated or plural fluorescent dyes are bound to each single protein or gene; therefore, the size of the signals (dots in an image) is not constant and, when dots form aggregates, it is unclear as to how many HER2 protein molecules correspond to each aggregate. According to the above-described quantification principle of the present invention, counting of the number of fluorescent nanoparticles is synonymous to counting the number of specific breast cancer-related proteins, and it is thus believed that an accurate measurement of the number of breast cancer-related proteins leads to an accurate understanding of the properties of the breast cancer of a patient as well as highly accurate prediction of pCR.

Incidentally, the above-described hypothesis relating to the quantification principle of the present invention, that is, the point that a single breast cancer-related protein is marked with a single fluorescent nanoparticle, has been recently demonstrated by observation results obtained using an atomic force microscope (AFM). As shown in the below-described Reference Example, the present inventors constructed the evaluation system shown in FIG. 24 and measured the binding force between streptavidin bound to the PID surface and solid-phase immobilized biotin by performing an binding assay. As a result, the binding force was concluded to be 40 pN as the difference between the values measured under the condition I (FIG. 25C) and the values measured under the condition II (FIG. 25D). This difference was equivalent to the values of the binding force between a single streptavidin molecule and a single biotin molecule that have been reported by many researchers. In other words, as disclosed in the below-described Examples, even in such an embodiment where streptavidin-modified PIDs are allowed to bind to biotin-modified secondary antibodies indirectly bound to HER2, a presumption that a single PID is bound to a single HER protein can be sufficiently substantiated.

From the above-described findings, the present inventors discovered that whether or not a breast cancer patient to be subjected to a preoperative therapy will exhibit pCR can be predicted by collecting a sample from the breast cancer patient, quantifying the expression level of HER2 or other breast cancer-related protein in accordance with an IHC-PID method and then comparing the thus quantified value or a value reduced therefrom, such as a ratio, with a prescribed threshold value drawn in advance from the above-described findings. In addition, with regard to the distribution pattern of a histogram representing the HER2 expression level determined by the IHC-PID method, the present inventors discovered that whether or not the breast cancer patient will exhibit pCR can be predicted by evaluating whether or not the distribution pattern conforms well to that of a pCR group drawn in advance from the above-described findings. Furthermore, the present inventors also discovered that pCR can be predicted with high accuracy when the prediction result obtained by comparing the above-described quantified value or the like with a threshold value and the prediction result obtained by comparing the histogram distribution patterns are combined and both of these results yield a prediction that pCR will be attained.

Particularly, it is novel to evaluate a breast cancer-related molecule by measuring the expression level of a specific protein contained in a sample (sliced tissue section) prepared from a breast cancer tissue of a breast cancer patient to be subjected to a preoperative therapy in terms of the number of bright spots representing the fluorescence signal of fluorescent nanoparticles or the number of particles, subsequently performing the characteristic step of preparing a histogram of the thus measured values, that is, preparing a histogram by plotting the number of bright spots per cell or the number of particles per cell (average expression level) on the abscissa and the number of cells on the ordinate, and then stratifying the distribution pattern of the thus obtained histogram. It is an intriguing fact that this evaluation method can be an effective means for supporting the prediction of pathological complete response (pCR).

That is, the present invention encompasses the following inventions.

A test support method for supporting the prediction of pathological complete response (pCR) to preoperative therapy in breast cancer by using a breast cancer tissue section collected from a breast cancer patient, the test support method comprising the following steps [1], [2], and [3]:

Step [1]: A step of acquiring a fluorescence image of the breast cancer tissue section, which fluorescence image shows bright spots of fluorescent nanoparticles labeling one or more kinds of breast cancer-related proteins;

Step [2]: A step of acquiring, on the basis of the bright spots of the fluorescence image, at least one index relating to the expression level(s) of the breast cancer-related protein(s); and Step [3]: A step of acquiring information for predicting pCR by performing an analysis using the at least one index.

BRIEF DESCRIPTION OF THE DRAWINGS

The advantages and features provided by one or more embodiments of the invention will become more fully understood from the detailed description given hereinbelow and appended drawings which are given by way of illustration only, and thus are not intended as a definition of the limits of the present invention.

FIG. 1 shows, as disclosed in Example 1: a DAB-stained image (A), a PID-stained image (B), a hematoxylin-stained image (C), and a composite (D) of the PID-stained image and the hematoxylin-stained image, which images (A) to (D) represent one example of the breast cancer patents of the pCR group; and a DAB-stained image (E), a PID-stained image (F), a hematoxylin-stained image (G), and a composite (H) of the PID-stained image and the hematoxylin-stained image, which images (E) to (H) represent one example of the breast cancer patents of the non-pCR group.

FIG. 2 is a box plot showing the IHC-DAB color intensity (color intensity per unit tissue area) of HER2 protein for the pCR group and the non-pCR group as disclosed in Example 1.

FIG. 3 is a box plot showing the FISH score of the HER2 gene for the pCR group and the non-pCR group as disclosed in Example 1.

FIG. 4 is a box plot showing the PID score (number of PID particles per unit tissue area) of HER2 protein for the pCR group and the non-pCR group as disclosed in Example 1.

FIG. 5 is a box plot showing the IHC-DAB color intensity (color intensity per unit tissue area) of HER2 protein for the group surviving for at least 100 months post-surgery (corresponding to the pCR group) and the group surviving for less than 100 months post-surgery (corresponding to the non-pCR group) as disclosed in Example 2.

FIG. 6 is a box plot showing the FISH score of the HER2 gene for the group surviving for at least 100 months post-surgery and the group surviving for less than 100 months post-surgery as disclosed in Example 2.

FIG. 7 is a box plot showing the PID score (number of PID particles per unit tissue area) of HER2 protein for the group surviving for at least 100 months post-surgery and the group surviving for less than 100 months post-surgery as disclosed in Example 2.

FIG. 8 is an ROC curve (receiver operating characteristic curve) for the PID scores of HER2 protein as disclosed in Example 2.

FIG. 9 is a box plot showing the PID score (number of PID particles per unit tissue area) of HER1 protein for the group surviving for at least 100 months post-surgery and the group surviving for less than 100 months post-surgery as disclosed in Example 2.

FIG. 10 is a box plot showing the PID score ratio of HER2/HER1 for the group surviving for at least 100 months post-surgery and the group surviving for less than 100 months post-surgery as disclosed in Example 2.

FIG. 11 is a drawing that explains the process of preparing a histogram from the PID scores of HER2 protein as disclosed in Examples 3 and 4.

FIG. 12 (FIGS. 12-1 and 12-2) shows histograms prepared from the PID scores of HER2 protein as disclosed in Example 3.

FIG. 13 is a box plot showing the IHC-DAB color intensity (color intensity per unit tissue area) of HER2 protein for the pCR group and the non-pCR group as disclosed in Example 4.

FIG. 14 is a box plot showing the FISH score of the HER2 gene (HER2 gene average copy number) for the pCR group and the non-pCR group as disclosed in Example 4.

FIG. 15 is a box plot showing the PID score (number of PID particles per unit tissue area) of HER2 protein for the pCR group (n=48) and the non-pCR group (n=33) as disclosed in Example 4.

FIG. 16 is a box plot showing the PID score (number of PID particles per cell) of HER2 protein for the pCR group and the non-pCR group as disclosed in Example 4.

FIG. 17 is an ROC curve (receiver operating characteristic curve) for the PID score (number of PID particles per cell) of HER2 protein as disclosed in Example 4.

FIG. 18 is a box plot showing the PID score (number of PID particles per cell) of HER1 protein as disclosed in Example 4.

FIG. 19 is a box plot showing the PID score (number of PID particles per cell) ratio of HER2/HER1 for the pCR group and the non-pCR group as disclosed in Example 4.

FIG. 20 is a box plot showing the PID score (number of PID particles per cell) of HER3 protein as disclosed in Example 4.

FIG. 21 is a box plot showing the PID score (number of PID particles per cell) ratio of HER2/HER3 for the pCR group and the non-pCR group as disclosed in Example 4.

FIG. 22 is a box plot showing the PID score (number of PID particles per cell) ratio of HER3/HER2 for the pCR group and the non-pCR group as disclosed in Example 4.

FIG. 23 is a flow chart of the test support method according to one embodiment of the present invention.

FIG. 24 is a schematic diagram of the evaluation system shown in Reference Example.

FIG. 25 is a set of drawings that relate to the evaluation of the binding force between a single PID particle and biotin having a specific density as shown in Reference Example 1, wherein (A) is a schematic diagram of AFM measurement; (B) is an SEM image of an AFM cantilever coated with PIDs (the binding force of the PID particle (arrow) positioned at the tip of the AFM cantilever was measured); (C) is a histogram based on the measured values of (binding force—distance) under the condition I; (D) is a histogram based on the measured values of (binding force—distance) under the condition II; and (E) is a histogram based on the measured values of (binding force—distance) under the condition III.

DETAILED DESCRIPTION OF EMBODIMENTS

Hereinafter, one or more embodiments of the present invention will be described with reference to the drawings. However, the scope of the invention is not limited to the disclosed embodiment.

The test support method of the present invention is a test support method for supporting the prediction of pathological complete response (pCR) to preoperative therapy in breast cancer by using a sample of a breast cancer tissue collected from a breast cancer patient to be subjected to a preoperative chemotherapy, the test support method basically comprising the following steps [1] to [3]:

Step [1]: the step of acquiring a fluorescence image of the breast cancer tissue section, which fluorescence image shows bright spots of fluorescent nanoparticles labeling one or more kinds of breast cancer-related proteins;

Step [2]: the step of acquiring at least one index relating to the expression level(s) of the breast cancer-related protein(s) on the basis of the bright spots of the fluorescence image; and Step [3]: the step of acquiring information for predicting pCR by performing an analysis using the above-described at least one index.

The breast cancer patient from whom a sample of a breast cancer tissue is collected may be in a state of before the start of the preoperative chemotherapy, or in a state of after the start but before the completion of the preoperative chemotherapy (that is, in the middle of the preoperative chemotherapy).

The test support method of the present invention can be generally classified into two types based on the characteristic features of its preferred embodiments.

In a first embodiment of the test support method, two or more kinds of breast cancer-related proteins including at least HER2, that is, HER2 and at least one other breast cancer-related protein are the labeling targets of the fluorescent nanoparticles in the step [1]. Further, in the step [2], numerical values representing the expression levels of each of the two or more kinds of breast cancer-related proteins, that is, a numerical value representing the expression level of HER2 and a numerical value representing the expression level of at least one other breast cancer-related protein are acquired, or a numerical value calculated from a combination of these numerical values, for example, a numerical value calculated by dividing the numerical value representing the expression level of HER2 by the numerical value representing the expression level of other breast cancer-related protein, is acquired. Then, in the step [3], an analysis which comprises comparing the thus acquired numerical value(s) as the above-described index with a prescribed threshold value(s) is performed.

That is, the first embodiment of the test support method of the present invention comprises the following steps [1], [2] and [3]:

Step [1]: the step of acquiring a fluorescence image of a breast cancer tissue section, which image shows bright spots of fluorescent nanoparticles labeling two or more kinds of breast cancer-related proteins including at least HER2;

Step [2]: the step of acquiring, on the basis of the bright spots of the fluorescence image, numerical values representing the expression levels of each of the two or more kinds of breast cancer-related proteins or a numerical value calculated from a combination of these numerical values as the above-described index; and Step [3]: the step of acquiring information for predicting pCR by performing an analysis which comprises comparing the thus acquired numerical value(s) with a prescribed threshold value(s).

In a second embodiment of the test support method, at least a histogram based on the expression level of the breast cancer-related protein per cell is prepared in the step [2], and an analysis which comprises at least classifying the distribution pattern of the histogram is performed in the step [3].

That is, the second embodiment of the test support method of the present invention comprises the following steps [1], [2] and [3]:

Step [1]: the step of acquiring a fluorescence image of a breast cancer tissue section, which image shows bright spots of fluorescent nanoparticles labeling one or more kinds of breast cancer-related proteins;

Step [2]: the step of acquiring, as the above-described index, at least a histogram based on the expression level of the breast cancer-related protein per cell, which histogram is prepared on the basis of the bright spots of the fluorescence image; and Step [3]: the step of acquiring information for predicting pCR by performing an analysis which comprises at least classifying the distribution pattern of the histogram.

The test support method of the present invention may also take such an embodiment that combines the first and the second embodiments, that is, an embodiment comprising the following steps [1], [2] and [3] in which an analysis utilizing at least a histogram based on the expression level of HER2 per cell is performed:

Step [1]: the step of acquiring a fluorescence image of a breast cancer tissue section, which fluorescence image shows bright spots of fluorescent nanoparticles labeling one or more kinds of breast cancer-related proteins including at least HER2;

Step [2]: the step of acquiring, on the basis of the bright spots of the fluorescence image, at least a histogram based on the expression level of HER2 per cell as the above-described index; and Step [3]: the step of acquiring information for predicting pCR by performing an analysis which comprises at least classifying the distribution pattern of the histogram.

The test support method according to the above-described embodiments has a tremendous clinical significance in that it not only simply judges whether or not an anticancer drug (e.g., trastuzumab) should be applied to a patient as in a conventional HER2 test, but also is capable of predicting with high accuracy whether or not a patient administered with the drug will exhibit pCR.

Step [1]: Fluorescence Image Acquisition Step

The step [1] included in the test support method of the present invention is the step of acquiring a fluorescence image of a breast cancer tissue section, which image shows bright spots of fluorescent nanoparticles labeling at least one kind of breast cancer-related protein, for example, two or more kinds of breast cancer-related proteins including at least HER2 (first embodiment).

(Breast Cancer-Related Proteins)

The breast cancer-related proteins in the test support method of the present invention are proteins expressed by cells contained in a breast cancer tissue or proteins existing around such cells, which proteins relate to the actions and effects of an anticancer drug used in a preoperative chemotherapy of breast cancer. The breast cancer tissue includes not only breast cancer cells but also cells other than breast cancer cells, examples of which include immunocytes that interact with tumor cells such as breast cancer cells. The breast cancer-related proteins are not limited to proteins expressed by breast cancer cells as long as they relate to the actions and effects of an anticancer drug, and the breast cancer-related proteins may also be proteins expressed by a cell other than breast cancer cells.

The breast cancer-related proteins are, for example, among cancer cell growth factors, cancer cell growth factor receptors, cell surface antigens, vascular growth factors, vascular growth factor receptors, cytokines, cytokine receptors, immune checkpoint proteins, markers indicating cancer growth potential and the like, one relating to the actions and effects of an anticancer drug against breast cancer. Specific examples of the cancer cell growth factors and cancer cell growth factor receptors include HER1 (EGFR), HER2, HER3, HER4, IGFR, and HGFR. Specific examples of the cell surface antigens, vascular growth factors and vascular growth factor receptors include VEGF-A, VEGF-B, VEGF-C, VEGF-D, VEGF-E, PlGF-1, and PlGF-2. Specific examples of the cytokines and cytokine receptors include interferons, interleukins, G-CSF, M-CSF, EPO, SCF, EGF, FGF, IGF, NGF, PDGF, and TGF. Specific examples of the immune checkpoint proteins include CD40, TL1A, GITR-L, 4-188-L, CX4D-L, CD70, HHLA2, ICOS-L, CD85, CD80, MHC-II, PDL1, PDL2, VISTA, BTNL2, B7-H3, B7-H4, CD48, HVEM, CD40L, TNFRSF25, GITR, 4-188, OX40, CD27, TMIGD2, ICOS, CD28, TCR, LAG3, CTLA4, PD1, CD244, TIM3, BTLA, CD160, and LIGHT. Specific examples of the markers indicating cancer growth potential include Ki67. Ki67, which is a protein expressed in nuclei during cell division, is used for evaluating the growth potential and malignancy of breast cancer and various other tumors and, for example, a method of determining the cancer recurrence risk based on a combination of the number of Ki67-expressing cells or the Ki67 expression level in a breast cancer tissue and other information has been proposed (JP 2011-209220A).

In one preferred embodiment of the present invention, the breast cancer-related proteins are proteins that serve as the targets of a molecular target drug effective against breast cancer, and examples thereof include HER1 (EGFR), HER2, HER3, VEGFR, PD-L1, PD-1, CTLA-4, and Ki67. For example, a combination of HER2 and HER1 or HER3 is particularly preferred since highly reliable information can be acquired therefrom for the prediction of pCR by the analysis of the step [3].

In one preferred embodiment of the present invention, the breast cancer-related proteins are phosphorylated proteins, and examples thereof include HER1 (EGFR), HER2, HER3, and VEGFR. A phosphorylated-type protein can be quantified using an antibody which specifically recognizes only the phosphorylated-type protein among the breast cancer-related proteins in immunostaining. In cases where it is desired to quantify all of the breast cancer-related proteins regardless of whether they are of phosphorylated type or non-phosphorylated type, an antibody which recognizes the breast cancer-related proteins without discriminating these types may be used.

An anticancer drug used in preoperative chemotherapy of breast cancer is typically a molecular target drug which targets a specific breast cancer-related protein, and examples thereof include anti-HER2 humanized monoclonal antibodies that specifically bind to the extracellular domain of HER2, such as trastuzumab (registered trademark "Herceptin") and pertuzumab (registered trademark "Perjeta"); complexes of an anti-HER2 humanized monoclonal antibody and a drug (e.g., a tubulin polymerization inhibitor), such as trastuzumab emtansine (registered trademark "Kadcyla"); and tyrosine kinase inhibitors that target the intracellular kinase domains of HER1 (EGFR) and HER2, such as lapatinib tosilate hydrate (registered trademark "Tykerb"). These molecular target drugs may be used individually or in combination of a plurality thereof, and they may also be used in combination with a drug(s) other than a molecular target drug, such as a taxane-based drug (e.g., docetaxel or paclitaxel) and/or an anthracycline-based drug (e.g., doxorubicin or epirubicin).

(Fluorescent Nanoparticles)

The fluorescent nanoparticles may be non-integrated particles (inorganic phosphor) such as quantum dots or silica dots or may be particles in which a phosphor (e.g., a fluorescent dye or a quantum dot) is integrated into a matrix such as a resin (phosphor-integrated particles or phosphor-integrated dots: PIDs), as long as the particles can show bright spots indicating the presence of breast cancer-related proteins in a fluorescence image. Examples of the PIDs include fluorescent dye-integrated resin particles that are prepared using a fluorescent dye as the phosphor and a resin as the matrix; fluorescent dye-integrated silica particles that are prepared using a fluorescent dye as the phosphor and silica as the matrix; inorganic phosphor-integrated resin particles that are prepared using an inorganic phosphor as the phosphor and a resin as the matrix; and inorganic phosphor-integrated silica particles that are prepared using an inorganic phosphor as the phosphor and silica as the matrix. Thereamong, as the fluorescent nanoparticles used in the present invention, fluorescent dye-integrated resin particles that are prepared using a fluorescent dye (e.g., perylene diimide, pyrromethene, Sulforhodamine 101 or a hydrochloride thereof (Texas Red)) as the phosphor and a resin (e.g., a melamine resin or a styrene resin) as the matrix are preferred since such particles have excellent labeling performance and the like.

When phosphor-integrated particles (PIDs) are used as the fluorescent nanoparticles in the present invention, by controlling the size of the fluorescent nanoparticles in a prescribed range, the bright spots that indicate the PIDs labeling breast cancer-related proteins in a fluorescence image are allowed to have a certain size preferable for the quantification of expression level. From this standpoint, the average particle size of the PIDs is preferably 40 nm to 160 nm. The particle size of each PID can be determined by taking a photograph thereof using a scanning electron microscope (SEM), measuring the cross-sectional area of the resin particle for fluorescent labeling, and then calculating the particle size as the diameter of a circular area corresponding to the thus measured value (area-equivalent circle diameter). With regard to the average particle size and the variation coefficient of a group of PIDs, after measuring the particle diameter for each of a sufficient number (for example, 1,000) of the PIDs in the above-described manner, the average particle size can be calculated as the arithmetic mean of the thus measured values. The variation coefficient of a group of PIDs can be calculated the ratio of the standard deviation to the average particle size.

Breast cancer-related proteins can be directly or indirectly labeled with such fluorescent nanoparticles that are coupled with and modified by, for example, an antibody for each breast cancer-related protein (primary antibody, such as an anti-HER2 rabbit monoclonal antibody), an antibody for such a primary antibody (secondary antibody, such as an anti-rabbit IgG antibody), or avidin or an anti-hapten antibody (e.g., anti-digoxigenin antibody or anti-FITC antibody) that reacts with biotin or a hapten (e.g., digoxigenin or FITC) modifying the primary or secondary antibody. In order to approximate the number of the above-described modified fluorescent nanoparticles binding to a single breast cancer-related protein (average value) to 1 as close as possible, it is preferred to adjust the modification conditions of the fluorescent nanoparticles or the conditions of the substance to which the modified fluorescent nanoparticles bind.

In the first embodiment of the present invention, two or more kinds of breast cancer-related proteins including at least HER2, for example, HER2 and HER1 or HER2 and HER3, are labeled. In this case, it is preferred to simultaneously stain the respective breast cancer-related proteins on a single breast cancer tissue section using two or more kinds of fluorescent nanoparticles having different colors (maximum emission wavelengths). Fluorescence images showing bright spots of each breast cancer-related protein can be obtained as separate fluorescence images by irradiating excitation wavelengths that correspond to the respective fluorescent nanoparticles through a filter transmitting the emission wavelength corresponding to each fluorescent nanoparticle (filter that do not transmit other emission wavelengths). In cases where this embodiment is not adopted, for example, fluorescence images of each breast cancer-related protein can also be obtained by staining each breast cancer-related protein with fluorescent nanoparticles on each of two or more adjacent thin sections prepared from a single formalin-fixed paraffin-embedded tissue block.

Basic embodiments of a method of directly or indirectly labeling a protein of interest (breast cancer-related protein in the present invention) with fluorescent nanoparticles (particularly an IHC-PID method using PIDs as a fluorescent label) are known from WO 2012/029342 (Patent Document 1), WO 2013/146741 (Patent Document 2) and other patent documents and non-patent documents, and the method can be carried out in an embodiment that conforms to a case of performing a conventional general pathological diagnosis using a specimen slide.

In the present invention, since fluorescent nanoparticles are used for labeling a breast cancer-related protein(s), there is no such a problem that a dye generated by an enzyme reaction is mixed with a staining agent used for morphological observation as in a conventional IHC method. Therefore, a staining treatment of a breast cancer-related protein (s) with fluorescent nanoparticles can be performed together with a staining treatment for cell morphological observation on a single tissue section. Such an embodiment is preferred since, for example, the expression level of a breast cancer-related protein per cell can be obtained as a measured value (i) in the below-described step [2], and the basic matters of this embodiment are described in, for example, WO 2013/035688.

Further, instead of using a staining agent for morphological observation, fluorescent nanoparticles may also be used for labeling a membrane protein other than breast cancer-related proteins that is constitutively expressed on cell membranes (reference biological substance, such as ATPase, cadherin, cytokeratin or EpCAM) so as to obtain a fluorescence image in which regions of cell membranes are indicated with fluorescent bright spots. In this case, a breast cancer-related protein(s) and the above-described reference biological substance are stained on a single tissue section by two kinds of fluorescent nanoparticles having different maximum excitation wavelengths and maximum emission wavelengths, so that bright spots of the breast cancer-related protein(s) and those of the above-described reference biological substance can be obtained as separate fluorescence images. The basic matters of such an embodiment are described in, for example, WO 2015/146896.

(Breast Cancer Tissue Section)

The breast cancer tissue section used in the present invention is prepared from a human-derived breast cancer tissue. In the present specification, the term "breast cancer tissue section" refers to one obtained by thin-slicing a sample using a microtome or the like, and the term "sample" refers to one obtained by collecting a breast cancer tissue or a breast cancer cell-containing region from a breast cancer patient or an experimental animal using a biopsy needle and subsequently processing the thus collected tissue or region into a formalin-fixed paraffin-embedded tissue block in accordance with a conventional method. The experimental animal is preferably an experimental animal transplanted with a breast cancer tissue or breast cancer cells derived from human.

Experimental animals transplanted with a cancer tissue or cancer cells are generally referred to as "tumor-bearing animals". Tumor-bearing animals encompass: $0^{th}$-generation experimental animals that have been transplanted with a tumor tissue or tumor cells collected from a human or with human-derived tumor cells established as a cultured cell line; and $n^{th}$-generation ($n \geq 1$) experimental animals that have been transplanted with a tumor tissue or tumor cells grown in the body of a $(n-1)^{th}$-generation experimental animal, which tumor tissue or tumor cells are originated from those transplanted into such a $0^{th}$-generation experimental animal as described above. These experimental animals can be prepared by a known method. For example, in the cases of mice, a variety of tumor-bearing model mice, such as CDX (cell line-derived xenograft) model mice, PDX (patient-derived xenograft) model mice, human xenograft model mice, immuno-avatar model mice, hemato-lymphoid humanized model mice and immune-PDX model mice, can be prepared, and an environment where ready-to-use tumor-bearing model mice are available for purchase has been established as well. Meanwhile, tumor-bearing model mice that have been transplanted with cultured cells derived from tumor cells collected from a patient are more classical and can be easily prepared.

Examples of experimental animals that can be used in the present invention include $0^{th}$-generation experimental animals that have been transplanted with a breast cancer tissue or breast cancer cells collected from a breast cancer patient; and $n^{th}$-generation ($n \geq 1$) experimental animals that have been transplanted with a breast cancer tissue or breast cancer cells grown in the body of a $(n-1)^{th}$-generation experimental animal, which breast cancer tissue or breast cancer cells are originated from those transplanted in such a $0^{th}$-generation experimental animal as described above.

Step [2]: Index Acquisition Step

The step [2] included in the test support method of the present invention is the step of acquiring, on the basis of the bright spots of the fluorescence image acquired in the step [1], numerical values representing the expression levels of each of the above-described two or more kinds of breast cancer-related proteins (first embodiment), or at least a histogram based on the expression levels of the breast cancer-related proteins per cell (second embodiment), as the above-described index.

(Index)

Examples of an index relating to the expression level of a breast cancer-related protein include: (I) the expression level of a breast cancer-related protein per cell (average value); (II) the expression level of a breast cancer-related protein per unit tissue area (average value); (III) a histogram based on the expression level of a breast cancer-related protein per cell; and (IV) a distribution curve based on the expression level of a breast cancer-related protein per cell.

In order to obtain the above-described indices, specifically, on the basis of bright spots of a fluorescence image, for example, (i) the expression level of a breast cancer-related protein per cell, (ii) the total number of cells for which the expression level was measured, (iii) the expression level of the breast cancer-related protein in cells that are contained in a prescribed region of a breast cancer tissue, and (iv) the area of the region for which the expression level was measured can be measured. By using the above-described measurement values of (i) and (ii), the above-exemplified index (I), which is the expression level of a breast cancer-related protein per cell (average value), can be calculated. By using the above-described measurement values of (iii) and (iv), the above-exemplified index (II), which is the expression level of a breast cancer-related protein per unit area of a breast cancer tissue (average value), can be calculated. Further, by using the above-described measured value of (i), the above-exemplified index (III) or (IV), which is a histogram or a distribution curve, can be prepared.

The (i) expression level of a breast cancer-related protein per cell can be measured by, for example, in the step [1], immunostaining a tissue section (specimen slide) with fluorescent nanoparticles and also staining the tissue section with a staining agent for morphological observation (e.g., hematoxylin or eosin) such that the shape of the cells can be specified. In this case, in the step [1], first, by observation and photographing in a dark field that are performed while irradiating an excitation light having a prescribed wavelength that corresponds to the fluorescent nanoparticles, an image showing the fluorescent nanoparticles labeling the breast cancer-related protein as bright spots is obtained. Meanwhile, by observation and photographing in a bright field, an image stained with the staining agent for morphological observation in such a manner to show the shape of the cells is also obtained. In the step [2], by superimposing these two images with each other through image processing, the number of bright spots labeling the expressed breast cancer-related protein can be measured for individual cells that are contained in the entirety of the images or a specific region (e.g., only in the tumor tissue) of the images. Those cells containing no bright spot and those cells having bright spots extracellularly are not included in the measurement.

The number of bright spots can be measured for any number of cells or any area of a region; however, in consideration of obtaining reasonable values (statistically reasonable values in particular) in the calculation of the indices of (i) and (ii) and the preparation of a histogram and a distribution curve as the indices of (iii) and (iv), it is appropriate to measure the number of bright spots for a sufficiently large number of cells or area of a region. The number of bright spots may be measured on a single specimen slide (tissue section) for a single visual field or a prescribed number of cells contained therein, or for two or more visual fields or a prescribed number of cells that are contained in each of the visual fields.

The expression level of a breast cancer-related protein may be indicated by the number of bright spots measured in the above-described manner or by the number of particles constituting bright spots that can be calculated from the number of the bright spots; however, from the standpoint of improving the accuracy of the analysis in the step [3], the latter is more preferred. Since a single bright spot may be constituted by fluorescence emitted by plural fluorescent nanoparticles, the number of fluorescent nanoparticles constituting a certain single bright spot can be calculated by dividing the brightness (luminance or fluorescence intensity) of the single bright spot by the brightness per fluorescent nanoparticle that has been separately measured in advance.

The index (I), which is the expression level of a breast cancer-related protein per cell (average value), can be calculated by using the measurement value (i): the expression level of the breast cancer-related protein per cell and the measurement value (ii): the total number of cells for which the expression level was measured, that is, by dividing the sum of the measurement values (i) by the measurement value (ii).

The index (II), which is the expression level of a breast cancer-related protein per unit area of a breast cancer tissue (average value), can be calculated by using the measurement value (iii): the expression level of the breast cancer-related protein in cells (the breast cancer-related protein existing within the shapes of cells indicated by a staining agent for morphological observation) that are contained in a prescribed region of a breast cancer tissue (which region may be the entirety or a part of a visual field) and the measurement value (iv): the area of the region for which the expression level was measured, that is, by dividing the measurement value (iii) by the measurement value (iv).

The index (III), which is a histogram based on the expression level of a breast cancer-related protein per cell, can be prepared by first, based on the measurement value (i): the expression level of the breast cancer-related protein per cell, setting a plurality of classes having a certain desired width for the expression level, subsequently calculating the number (frequency) of cells belonging to each class, and then plotting the former on the abscissa and the latter on the ordinate. The classes on the abscissa can consist of, for example, as shown in Examples described in the present specification, a total of 41 classes formed by dividing the number of bright spots of 0 to 400 at intervals of 10 bright spots.

The index (IV), which is a distribution curve based on the expression level of a breast cancer-related protein per cell, can also be prepared by, based on the measurement value (i): the expression level of the breast cancer-related protein per cell, plotting the expression level on the abscissa (without such intervals of a histogram) and the number (frequency) of cells corresponding to each expression level on the ordinate.

Step [3]: Step of Acquiring Information for Prediction of pCR

The step [3] included in the test support method of the present invention is the step of acquiring information for predicting pCR by performing an analysis using at least one index described above, for example, an analysis which comprises comparing the numerical value(s) obtained in the step [2] with a prescribed threshold value(s) (first embodiment) or an analysis which comprises at least classifying the distribution pattern of above-described histogram (second embodiment).

The "analysis using at least one index" is not particularly restricted as long as it can yield information having a certain reliability based on which whether or not pCR will be attained can be predicted.

In the step [3] of one preferred embodiment of the present invention, an analysis of classifying the distribution pattern of a histogram prepared based on the expression level of at least HER2 per cell is performed, and other analyses are also performed as required. For this purpose, in the step [1], one or more kinds of breast cancer-related proteins including at least HER2 may be labeled with fluorescent nanoparticles and, in the step [2], a histogram based on the expression level of at least HER2 per cell may be acquired as an index and, as required, other numerical values or histograms may also be acquired as indices.

In the step [3] of one preferred embodiment of the present invention, an analysis which comprises comparing the value of either (a) ratio of the numerical value representing the expression level of HER2 with respect to the numerical value representing the expression level of HER1 (HER2/HER1) or (b) a ratio of the numerical value representing the expression level of HER2 with respect to the numerical value representing the expression level of HER3 (HER2/HER3) with a prescribed threshold value is performed. For this purpose, in the step [1], HER2 and HER1 or HER3 may be labeled with fluorescent nanoparticles (as required, other breast cancer-related proteins may further be labeled with fluorescent nanoparticles) and, in the step [2], the numerical values representing the expression level of HER2 and that of HER1 or HER3 may be obtained and the above-described ratio thereof may be calculated (as required, an index relating to other breast cancer-related protein may also be acquired).

In the step [3] of one preferred embodiment of the present invention, (a) an analysis of comparing a numerical value representing the expression level of HER2 with a prescribed threshold value and (b) an analysis of classifying the distribution pattern of a histogram prepared based on the expression level of HER2 per cell are performed in combination. For this purpose, in the step [1], HER2 may be labeled with fluorescent nanoparticles (as required, other breast cancer-related proteins may further be labeled with fluorescent nanoparticles) and, in the step [2], (a) the numerical value representing the expression level of HER2 may be obtained and (b) a histogram based on the expression level of HER2 per cell may be prepared (as required, an index relating to other breast cancer-related protein may also be acquired).

In cases where an analysis that uses numerical values representing the expression levels of breast cancer-related proteins as indices is performed in the step [3], the method of the analysis is not particularly restricted; however, typically, as described above, the numerical values are each compared to a prescribed threshold value (cut-off value) that is set in advance. In this case, diagnostically useful information that allows to predict whether or not a human or experimental animal from which a sample is collected will exhibit pCR as a result of performing a preoperative chemotherapy on the basis of whether the index values and the like are larger than (or not smaller than) or smaller than (not larger than) the respective threshold values.

Whether an index value or the like larger than a threshold value or an index value or the like smaller than a threshold value gives a prediction that pCR will be attained (conversely, whether an index value or the like smaller than a threshold value or an index value or the like larger than a threshold value gives a prediction that pCR will not be attained) is variable depending on the type of the index value or the like. For example, when the expression level of HER2 protein per unit area of a breast cancer tissue is used as the numerical value representing the expression level of HER2, it is predicted that pCR will be attained if the expression level is greater than a threshold value. Further, also when the ratio of numerical value representing the expression level of HER2/numerical value representing the expression level of HER1 or the ratio of numerical value representing the expression level of HER2/numerical value representing the expression level of HER3 is used, it is predicted that pCR will be attained if the value of the ratio is greater than a threshold value. This is believed to reflect the fact that the use of an anticancer drug targeting HER2 as a preoperative chemotherapy shows superior efficacy for a higher expression level of HER2 and this leads to an increased probability of attaining pCR. Generally speaking, in a comparison of the results of a pCR group and those of a non-pCR group as described below, when the pCR group has a statistically significantly higher value (the non-pCR group has a statistically significantly lower value), it is predicted that pCR will be attained if the value is larger than the threshold value, whereas when the pCR group has a statistically significantly lower value (the non-pCR group has a statistically signifi-cantly higher value), it is predicted that pCR will be attained if the value is smaller than the threshold value.

A threshold value (cut-off value) used in such an analysis can be drawn by, for those samples collected from plural breast cancer patients who eventually exhibited pCR (pCR group) and those samples collected from plural breast cancer patients who did not eventually exhibit pCR (non-pCR group) among samples collected prior to or in the middle of a preoperative chemotherapy, acquiring the numerical value representing the expression level of a specific breast cancer-related protein contained in each sample by an IHC-PID method and subsequently comparing the results of the pCR group with those of the non-pCR group. For example, when the expression level of HER2 protein per unit tissue area is used as an index value, it is ideal to set the threshold value such that as many as possible samples included in the pCR group have an index value larger than the threshold value (that is, the sensitivity is improved) and as less as possible samples included in the non-pCR group have an index value not larger than the threshold value (that is, the specificity is improved). Since a change in the threshold value leads to a change in the sensitivity and the specificity, it is desired to employ a value adjusted (optimized) to attain a good balance thereof as the threshold value of the step [3].

Meanwhile, in cases where an analysis that uses a histogram prepared based on the expression level of a breast cancer-related protein per cell as an index is performed in the step [3], the method of the analysis is not particularly restricted; however, typically, as described above, the distribution pattern of the histogram is classified, that is, the distribution pattern of the histogram is compared to several distribution patterns established in advance and it is determined to which of them the distribution pattern of the histogram correspond. For example, a histogram prepared based on the expression level of HER2 per cell can be classified into one of the following four distribution patterns: (A) a distribution pattern having a peak at the number of bright spots=0; (B) a unimodal distribution pattern in which the peak is shifted to the right; (C) a bimodal or multimodal distribution pattern; and (D) a distribution pattern with distribution over a wide range of classes. It is predicted that pCR will be attained when the distribution pattern of the histogram corresponds to the above-described (B), (C) or (D) (that is, a pattern with a small number of cells having no bright spot), while it is predicted that pCR will not be attained when the distribution pattern of the histogram corresponds to the above-described (A).

The distribution pattern in such an analysis can be classified as described above by, for example, comparing a histogram of the pCR group and that of a non-pCR group and identifying the distribution pattern to which as many as possible samples included in the pCR group (that is, high sensitivity) and as less as samples included in the non-pCR group (that is, low specificity) correspond while focusing on the mode and the like of the distribution peak(s) and, as required, referring to the numerical values such as average, median and variance (CV).

Further, also in cases where a distribution curve is prepared by continuously (without any division as in a histogram) plotting the expression level of the subject breast cancer-related protein per cell on the abscissa and plotting the number of cells corresponding to each expression level on the ordinate in place of the above-described histogram, it may be possible to perform the same analysis.

Although embodiments of the present invention have been described and illustrated in detail, the disclosed embodiments are made for purposes of illustration and example only and not limitation. The scope of the present invention should be interpreted by terms of the appended claims.

EXAMPLES

[Preparation Example 1] Preparation of Biotin-Modified Anti-Rabbit IgG Antibody

In a 50 mM Tris solution, 50 ng of an anti-rabbit IgG antibody (clone: LO-RG-1) to be used as a secondary antibody was dissolved. To the resulting solution, a DTT (dithiothreitol) solution was added to a final concentration of 3 mM, and the resultant was mixed and allowed to react at 37° C. for 30 minutes. Then, the thus obtained reaction solution was passed through a desalting column "ZEBA (trademark) Desalt Spin Columns" (manufactured by Thermo Fisher Scientific K.K., Cat. #89882) to purify a DTT-reduced secondary antibody. An antibody solution was prepared by dissolving 200 µL of the whole amount of the thus purified antibody in a 50 mM Tris solution. Meanwhile, a linker reagent "Maleimide-$PEG_2$-Biotin" (manufactured by Thermo Fisher Scientific K.K., 21901BID) was adjusted with DMSO to a concentration of 0.4 mM. Then, 8.5 µL of this linker reagent solution was added to the antibody solution, and the resultant was mixed and allowed to react at 37° C. for 30 minutes, whereby biotin was bound to the anti-rabbit IgG antibody via a PEG chain. The resulting reaction solution was purified through a desalting column. The absorbance of the thus desalted reaction solution was measured at a wavelength of 300 nm using a spectrophotometer ("F-7000", manufactured by Hitachi High-Technologies Corporation) to determine the concentration of the protein (biotin-modified secondary antibody) contained in the reaction solution. The reaction solution was adjusted with a 50 mM Tris solution to have a biotin-modified secondary antibody concentration of 250 µg/mL, and the resulting solution was used as a biotin-modified secondary antibody solution.

[Preparation Example 2] Preparation of Streptavidin-Modified Texas Red-Integrated Melamine Resin Particles As a fluorescent dye, 20.3 mg of a red fluorescent dye Texas Red was added to and dissolved in 22 mL of water. Then, to this solution, 2 mL of a 5% aqueous solution of an emulsifier for emulsion polymerization "EMULGEN" (registered trademark) 430 (polyoxyethylene oleyl ether, manufactured by Kao Corporation) was added. The resulting solution was heated to 70° C. with stirring on a hot stirrer, and 0.81 g of a melamine resin material, "NIKALAC MX-035" (manufactured by Nippon Carbide Industries Co., Inc.), was subsequently added thereto. To this solution, as a reaction initiator, 1,000 µL of a 10% aqueous solution of dodecylbenzenesulfonic acid (manufactured by Kanto Chemical Co., Inc.) was further added, and the resultant was heated with stirring at 70° C. for 50 minutes. Thereafter, the resultant was further heated with stirring at 90° C. for 20 minutes.

The resulting dispersion of Texas Red-integrated melamine resin particles was washed with pure water so as to remove impurities, such excess resin material and fluorescent dye. Specifically, the dispersion was centrifuged at 20,000 G for 15 minutes using a centrifugal machine "Micro Refrigerated Centrifuge 3740" (manufactured by Kubota Corporation) and, after removing the resulting supernatant, the precipitates were re-dispersed by adding ultrapure water and irradiating an ultrasonic wave thereto. The centrifugation, the removal of supernatant and the washing by re-dispersion in ultrapure water were repeated five times. By the above-described processes, Texas Red-integrated melamine resin particles (excitation wavelength=590 nm, emission wavelength=620 nm) were prepared.

Then, 0.1 mg of the thus obtained Texas Red-integrated melamine resin particles was dispersed in 1.5 mL of ethanol, and 2 µL of aminopropyltrimethoxysilane ("LS-3150", manufactured by Shin-Etsu Chemical Co., Ltd.) was added thereto. The resultant was allowed to react for 8 hours, whereby a surface amination treatment of converting the hydroxyl groups existing on the surface of the resin particles to amino groups was performed.

These Texas Red-integrated melamine resin particles were adjusted with a phosphate-buffered physiological saline (PBS) containing 2 mM of ethylenediamine tetraacetic acid (EDTA) to a concentration of 3 nM. The resulting dispersion of the Texas Red-integrated melamine resin particles having the adjusted concentration was mixed with $SM(PEG)_{12}$ (succinimidyl-[(N-maleimidopropionamido)-dodecaethylene glycol]ester, manufactured by Thermo Fisher Scientific K.K.) to a final concentration of 10 mM, and the resultant was allowed to react at 20° C. for 1 hour, whereby a mixture containing Texas Red-integrated melamine resin particles having maleimide group-modified surfaces was obtained.

This mixture was centrifuged at 10,000 G for 20 minutes, and the resulting supernatant was removed. The precipitates were subsequently dispersed by adding thereto PBS containing 2 mM of EDTA, and the resulting dispersion was centrifuged again. After repeating the above-described washing by the same procedure three times, maleimide group-modified Texas Red-integrated melamine resin particles were recovered.

Meanwhile, after allowing streptavidin (manufactured by Wako Pure Chemical Industries, Ltd.) to react with N-succinimidyl-S-acetylthioacetate (SATA), a thiol group was introduced to this streptavidin by performing a known hydroxylamine treatment for deprotection of S-acetyl group. Then, the resultant was subjected to gel filtration to separately prepare streptavidin capable of binding to fluorescent dye-integrated particles.

The above-described maleimide-modified Texas Red-integrated melamine resin particles and thiol group-introduced streptavidin were mixed in PBS containing 2 mM of EDTA and allowed to react at room temperature for 1 hour, whereby they (maleimide group and thiol group) were bound with each other. Then, the reaction was terminated with an addition of 10 mM mercaptoethanol. After concentrating the resulting solution using a centrifugation filter (φ=0.65 µm), unreacted streptavidin and the like were removed using a gel-filtration column for purification to obtain streptavidin-modified Texas Red-integrated melamine resin particles.

[Preparation Example 3] Preparation of Streptavidin-Modified Perylene Diimide-Integrated Melamine Resin Particles Streptavidin-modified perylene diimide-integrated melamine resin particles (excitation wavelength=590 nm, emission wavelength=620 nm) were obtained in the same manner as in Preparation Example 2, except that perylene diimide was used in place of Texas Red.

[Preparation Example 4] Preparation of Anti-HER1 Antibody-Modified Pyrromethene-Integrated Melamine Resin Particles (Green Fluorescent Nanoparticles)

As a fluorescent dye, 14.4 mg of a green fluorescent dye Pyrromethene 556 was added to and dissolved in 22 mL of water. Then, to this solution, 2 mL of a 5% aqueous solution of an emulsifier for emulsion polymerization "EMULGEN" (registered trademark) 430 (polyoxyethylene oleyl ether, manufactured by Kao Corporation) was added. The resulting solution was heated to 70° C. with stirring on a hot stirrer, and 0.65 g of a melamine resin material, "NIKALAC MX-035" (manufactured by Nippon Carbide Industries Co., Inc.), was subsequently added thereto. To this solution, as a reaction initiator, 1,000 µL of a 10% aqueous solution of dodecylbenzenesulfonic acid (manufactured by Kanto Chemical Co., Inc.) was further added, and the resultant was heated with stirring at 70° C. for 50 minutes. Thereafter, the resultant was further heated with stirring at 90° C. for 20 minutes.

The resulting dispersion of pyrromethene-integrated melamine resin particles was washed with pure water so as to remove impurities, such excess resin material and fluorescent dye. Specifically, the dispersion was centrifuged at 20,000 G for 15 minutes using a centrifugal machine "Micro Refrigerated Centrifuge 3740" (manufactured by Kubota Corporation) and, after removing the resulting supernatant, the precipitates were re-dispersed by adding ultrapure water and irradiating an ultrasonic wave thereto. The centrifugation, the removal of supernatant and the washing by re-dispersion in ultrapure water were repeated five times. By the above-described processes, pyrromethene-integrated melamine resin particles (excitation wavelength=490 nm, emission wavelength=520 nm) were prepared.

Maleimide was introduced to the thus obtained pyrromethene-integrated melamine resin particles using an NHS-PEG-maleimide reagent, and a thiolated anti-HER1 antibody was bound thereto, whereby anti-HER1 antibody-modified pyrromethene-integrated melamine resin particles were obtained.

[Example 1] Analysis Utilizing Numerical Values Representing Expression Levels of HER1, HER2 and HER3 (Corresponding to First Embodiment of Present Invention)

From breast cancer tissues collected from breast cancer patients by needle biopsy at Tohoku University Hospital during the period of 2011 to 2014, formalin-fixed paraffin-embedded tissue blocks (samples) were prepared in accordance with a conventional method, and these samples were each thin-sliced using a microtome to prepare specimen slides. Using the thus obtained specimen slides, DAB staining of the HER2 protein was performed using "HercepTest Kit" (manufactured by Dako Japan Co., Ltd.).

As a result of evaluating the IHC-DAB score, those patients diagnosed as HER2-positive were subjected to a preoperative chemotherapy of administering daunorubicin or doxorubicin, which is an anthracycline-based drug (topoisomerase inhibitor), for 3 months followed by administration of trastuzumab (trade name: Herceptin) and paclitaxel or docetaxel, which is a taxane-based drug (microtubule inhibitor), for 3 months. Thereafter, breast cancer tissue was removed by a surgery, and whether or not each patient exhibited pCR was assessed under a microscope based on the presence or absence of observed invasion of cancer cells in the primary focus and metastasis of cancer cells to lymph nodes.

Of 8 breast cancer patients who received the above-described preoperative chemotherapy, 6 patients exhibited pCR (pCR group) and 2 patients did not exhibit pCR (non-pCR group). Using the samples (formalin-fixed paraffin-embedded tissue blocks) of these breast cancer patients that were collected and preserved prior to the preoperative chemotherapy, PID staining was performed for each of HER2, HER1 and HER3 to acquired PID scores in accordance with the below-described procedures.

In addition, using the above-described samples, DAB staining of HER2 protein and FISH of the HER2 gene were also performed in parallel with the acquisition of PID scores. For the DAB staining, "HercepTest Kit" (manufactured by Dako Japan Co., Ltd.) was employed as described above. The DAB score on a four-point scale (0 to 3+) was evaluated in accordance with the conventional HER2 Testing Guidelines, and the DAB color intensity (IHC-DAB color intensity) per unit tissue area ($0.1$ $mm^2$) was measured using Aperio (manufactured by Leica Biosystems Nussloch GmbH). For the FISH, "PathVysion HWE2 DNA Probe Kit" (manufactured by Abbott Laboratories) was employed, and the number of observed bright spots was acquired as a FISH score (HER2 gene average copy number).

(1-1) PID Staining of HER2 and Acquisition of PID Score
(1-1-1) Specimen Pretreatment Step The above-described formalin-fixed paraffin-embedded tissue blocks derived from the tissues of the breast cancer patients were thin-sliced using a microtome to prepare specimen slides. These specimen slides were each deparaffinized and then washed by replacement with water. The thus washed specimen slides were subjected to a 15-minute autoclave treatment at 121° C. in 10 mM citrate buffer (pH 6.0), whereby an antigen retrieval treatment was performed. After the retrieval treatment, the specimen slides were each washed with PBS and then subjected to a 1-hour blocking treatment with 1% BSA-containing PBS.

(1-1-2) Immunostaining Step
(1-1-2-1) Primary Reaction Treatment of Immunostaining A primary reaction treatment liquid containing an anti-HER2 rabbit monoclonal antibody "4B5" (manufactured by Ventana Medical Systems, Inc.) at a concentration of 0.05 nM was prepared using 1% (w/w) BSA-containing PBS. The specimen slides prepared in the step (1-1-1) were each immersed in this primary reaction treatment liquid and allowed to react overnight at 4° C.

(1-1-2-2) Secondary Reaction Treatment of Immunostaining

A secondary reaction treatment liquid was prepared by further diluting the biotin-modified anti-rabbit IgG antibody solution prepared in Preparation Example 1 with 1% (w/w) BSA-containing PBS to a concentration of 6 µg/mL. The specimen slides subjected to the primary reaction treatment were each washed with PBS and subsequently immersed in this secondary reaction treatment liquid and allowed to react at room temperature for 30 minutes.

(1-1-2-3) Fluorescent Labeling Treatment of Immunostaining

A fluorescent labeling reaction treatment liquid was prepared by diluting the streptavidin-modified Texas Red-integrated melamine resin particles prepared in Preparation Example 2 to a concentration of 0.02 nM with a fluorescent nanoparticle diluent containing casein and BSA. The specimen slides subjected to the secondary reaction treatment were each immersed in this fluorescent labeling treatment liquid and allowed to react at room temperature for 3 hours under a neutral pH environment (pH 6.9 to 7.4).

(1-1-2-4) Staining Treatment for Morphological Observation

The specimen slides subjected to the fluorescent labeling treatment were each stained with Mayer's hematoxylin solution for 5 minutes to perform hematoxylin staining, and subsequently washed with 45° C. running water for 3 minutes.

(1-1-3) Specimen Post-Treatment Step

The thus immunostained specimen slides (stained slides) were subjected to a fixation-dehydration treatment where each slide was immersed in pure ethanol for 5 minutes four times. Subsequently, the stained slides were subjected to a clearing treatment where each slide was immersed in xylene for 5 minutes four times. Lastly, the stained slides were subjected to a mounting treatment where a mounting medium "Entellan New" (manufactured by Merck KGaA) was placed on each specimen and a cover glass was set thereon, whereby stained slides for observation were prepared.

(1-1-4) Evaluation Step (1-1-4-1) Observation and Image-Capturing Step

In this step, a fluorescence microscope "BX-53" (manufactured by Olympus Corporation) was used for irradiation of an excitation light and observation of emitted fluorescence, and a microscope digital camera "DP73" (manufactured by Olympus Corporation) attached to the fluorescence microscope was used for taking immunostained images (×400).

First, each stained slide was irradiated with an excitation light to cause the Texas Red, which was used for the fluorescent labeling of the protein of interest HER2, to emit fluorescence, and an immunostained image in this state was photographed (this process corresponds to the "fluorescence image acquisition step" in the test support method of the present invention). In this process, the wavelength of the excitation light was set at 575 to 600 nm using an excitation light optical filter installed in the fluorescence microscope, and the wavelength of the fluorescence to be observed was set at 612 to 692 nm using a fluorescence optical filter. The intensity of the excitation light in the observation and image capturing under the fluorescence microscope was set such that an irradiation energy of 900 W/cm$^2$ was provided in the vicinity of the center of the visual field. The exposure time for the image capturing was adjusted in such a range that does not cause saturation of the image brightness, and it was set at, for example, 4,000 μsec.

Next, by observation and image capturing in a bright field under the fluorescence microscope, stained images of cells stained with hematoxylin for morphological observation were photographed.

After immunostained images and stained images for morphological observation were captured in a single visual field as described above, the same operations were repeated in different visual fields to capture images in a total of five visual fields for each stained slide.

(1-1-4-2) Image Processing and Measurement Step

For the image processing in this step, an image processing software "ImageJ" (open source) was used.

The stained images for morphological observation were each processed to specify the shape of the cells (positions of the cell membranes) and superimposed with the respective immunostained images, and the bright spots representing the streptavidin-modified Texas Red-integrated melamine resin particles labeling the HER2 proteins expressed on the cell membranes were extracted and counted as the number of PID particles. Among the bright spots on the cell membranes, ones having a brightness of not less than a prescribed value were converted into the number of particles by dividing the brightness of such bright spots by the brightness per each of the Texas Red-integrated particles (PIDs). It is noted here that, since HER2 is not expressed in the interstitial cell region, those bright spots positioned inside the interstitial cells were processed as non-specific signals, that is, noise. Then, the number of the HER2-derived bright spots was measured in five visual fields for each stained slide, the thus measured values were each converted into the number of fluorescent nanoparticles per unit area (100 μm$^2$) as described above, and the average thereof was calculated as the "PID score" of each specimen slide (this process corresponds to the "index acquisition step" in the test support method of the present invention).

(1-2) PID Staining of HER1 and Acquisition of PID Score

PID staining of HER1 was performed and the PID scores were obtained in the same manner as in the above-described PID staining of HER2 and acquisition of PID scores, except that a primary reaction treatment liquid containing an anti-HER1 rabbit monoclonal antibody "5B7" (manufactured by Roche Diagnostics K.K., serial number: 790-4347) at a concentration of 0.05 nM was used in the step (1-1-2-1) in place of the primary reaction treatment liquid containing an anti-HER2 rabbit monoclonal antibody "4B5" (manufactured by Ventana Medical Systems, Inc.) at a concentration of 0.05 nM.

(1-3) PID Staining of HER3 and Acquisition of PID Score

PID staining of HER3 was performed and PID scores were obtained in the same manner as in the above-described PID staining of HER2 and acquisition of PID scores, except that a primary reaction treatment liquid containing an anti-HER3 rabbit monoclonal antibody "clone:RTJ2" (manufactured by ABR, serial number: MA1-860) at a concentration of 0.05 nM was used in the step (1-1-2-1) in place of the primary reaction treatment liquid containing an anti-HER2 rabbit monoclonal antibody "4B5" (manufactured by Ventana Medical Systems, Inc.) at a concentration of 0.05 nM.

(1-4) Analysis Results

FIG. 1 shows: a DAB-stained image (A), a PID-stained image (B), a hematoxylin-stained image (C), and a composite (D) of the PID-stained image and the hematoxylin-stained image, which images (A) to (D) represent one example of the breast cancer patients of the pCR group; and a DAB-stained image (E), a PID-stained image (F), a hematoxylin-stained image (G), and a composite (H) of the PID-stained image and the hematoxylin-stained image, which images (E) to (H) represent one example of the breast cancer patients of the non-pCR group. Both patients had an IHC-DAB score of 3+ and a FISH score of about 6; however, the preoperative chemotherapy yielded different results that the former exhibited pCR while the latter did not exhibit pCR. The PID scores of the former and the latter patients were 61.5 and 24.3, respectively.

(1-4-1) Relationship of IHC-DAB Color Intensity and FISH Score with pCR

For the pCR group and the non-pCR group, the color intensity (measured by AQUA) per unit tissue area (100 μm$^2$) obtained by the IHC-DAB staining and the FISH score are shown in FIGS. 2 and 3, respectively. Both of these figures were obtained for HER2. For both of the IHC-DAB color intensity and the FISH score, there was no difference in trend between the pCR group and the non-pCR group.

(1-4-2) Relationship Between PID Score of HER2 and pCR

FIG. 4 shows the PID scores (the calculated average number of PID particles per unit area (100 μm$^2$)) of HER2 protein for the pCR group and the non-pCR group. For the PID scores, a difference in trend was found between the pCR group and the non-pCR group.

It is easy to prepare an ROC curve (receiver operating characteristic curve) for the PID scores on the basis of the above-described results and to set an optimum cut-off value.

From these results, it is understood that, although whether or not pCR will be attained cannot be predicted prior to a preoperative chemotherapy using the IHC-DAB color intensity and the FISH score, the use of the PID score for HER2 protein enables to make the prediction with a certain accuracy even if the results are provided only for HER2.

[Example 2] Embodiment in which Numerical Values Representing Expression Levels of HER1 and HER2 are Acquired from Single Sample Slide (First Embodiment Using Double Staining)

PID staining of HER2 protein with a fluorescent labeling reaction treatment liquid that was prepared using the streptavidin-modified Texas Red-integrated melamine resin particles (excitation wavelength=590 nm, emission wavelength=620 nm) obtained in Preparation Example 2 and PID staining of HER1 protein with a fluorescent labeling reaction treatment liquid that was prepared using the anti-HER1 antibody-modified pyrromethene-integrated melamine resin particles (excitation wavelength=490 nm, emission wavelength=520 nm) obtained in Preparation Example 3 were performed on the same slide.

For the tissue slides, instead of using samples collected before the preoperative chemotherapy from plural breast cancer patients who eventually exhibited pCR (pCR group) and samples collected before the preoperative chemotherapy from plural breast cancer patients who did not exhibit pCR eventually (non-pCR group) as in Example 1, commercially available slides provided with clinical information (150-tissue sample array manufactured by Biomax, Inc., code: HBre-Duc150Sur-01; and breast cancer tissue sample slide manufactured by Asterand Bioscience) were purchased, and samples of a group surviving for at least 100 months post-surgery (this group corresponds to the pCR group) and samples of a group surviving for less than 100 months post-surgery (this group corresponds to the non-pCR group) were used.

For 49 of the above-described commercially available slides (25 sample spots of the patients surviving for at least 100 months post-surgery and 24 sample spots of the patients surviving less than 100 months post-surgery), the IHC-DAB color intensity of HER2 protein, the FISH score of the HER2 gene and the PID score of HER2 protein were measured in the same manner as in Example 1. For the results thereof, box plots are shown in FIGS. 5, 6 and 7. In Mann-Whitney U test, a significant difference was found between the pCR group and the non-pCR group in terms of the PID score of HER2 protein ($p<0.05$). FIG. 8 shows an ROC curve (receiver operating characteristic curve) for the PID score, which was prepared based on the above-described results. The optimum cut-off value was 51.3 and, in this case, the sensitivity (ordinate) was 68% and the specificity (abscissa) was 60%, meaning that the false-positive rate (1−specificity) was 40%.

Next, double staining with the streptavidin-modified Texas Red-integrated melamine resin particles and the anti-HER1 antibody-modified pyrromethene-integrated melamine resin particles was performed as follows. First, in accordance with the procedures up to (1-1-2-3) of Example 1, HER2 protein was fluorescently labeled with the streptavidin-modified Texas Red-integrated melamine resin particles. After this fluorescent labeling treatment on HER2 protein, HER1 protein was fluorescently labeled in the same manner as in (1-1-2-3) using the anti-HER1 antibody-modified pyrromethene-integrated melamine resin particles diluted with a fluorescent nanoparticle diluent to a concentration of 0.02 nM as a fluorescent labeling reaction treatment liquid. Thereafter, the same staining treatment for morphological observation as (1-1-2-4) was performed, and the same specimen post-treatment step as (1-1-3) was further performed, whereby stained slides were prepared.

The number of bright spots on the thus double-stained slides was measured as follows. First, in accordance with the procedures of the (1-1-4-1) observation and image-capturing step of Example 1, a fluorescence image of the streptavidin-modified Texas Red-integrated melamine resin particles labeling HER2 was photographed using an excitation light. Next, using a filter set manufactured by Semrock (optical filter for excitation light: 470 nm (30 nm in width), beam splitter: 495 nm, optical filter for fluorescence: 525 nm (50 nm in width)), a fluorescence image of the anti-HER1 antibody-modified pyrromethene-integrated melamine resin particles labeling HER1 was photographed. Then, the number of bright spots of HER2 and the number of bright spots of HER1 were measured in the same manner as in (1-1-4-2). Further, the PID score ratio of HER2/HER1 was calculated, and the results thereof were compared between the pCR group and the non-pCR group.

FIG. 9 is a box plot showing the PID scores of HER1 protein. Further, FIG. 10 is a box plot showing the PID score ratios of HER2/HER1, which was prepared based on the above-described results. In Mann-Whitney U test, a high level of significant difference was found between the pCR group and the non-pCR group ($p<0.001$).

From these results, it is believed that whether or not pCR will be attained can be predicted more accurately by using the PID score ratio of HER2/HER1 ($p<0.001$) as an index than using the PID score of HER2 alone ($p<0.05$) as an index.

[Example 3] Analysis Utilizing Distribution Pattern of Histogram Prepared Based on Expression Level of HER2 Per Cell (Corresponding to Second Embodiment of Present Invention)

For 8 samples derived from breast cancer tissues collected from breast cancer patients by needle biopsy at Tohoku University Hospital during the period of 2011 to 2014, the PID score of HER2 protein (number of PID bright spots per unit area) was obtained in the same manner as in the above-described (1-1) of Example 1. Based on the results thereof, histograms showing the PID score on the abscissa (a total of 41 classes each having a width of 10 PIDs) and the number of cells on the ordinate (a total number of cells in 5 visual fields on a single stained slide) were prepared. FIG. 11 is a drawing that explains the process of preparing the histograms, and FIG. 12 (FIGS. 12-1 and 12-2) shows the histograms that were actually prepared.

It was found that the thus prepared histograms can be classified into one of the following four patterns: (A) a pattern having a peak at the number of bright spots=0; (B) a unimodal pattern in which the peak is shifted to the right; (C) a bimodal or multimodal pattern; and (D) a pattern with distribution over a wide range of classes. In each pattern of (A) to (D), the number of the pCR group samples and that of the non-pCR group samples are as follows.

Pattern (A): pCR group=1, non-pCR group=2
Pattern (B): pCR group=3, non-pCR group=0
Pattern (C): pCR group=1, non-pCR group=0
Pattern (D): pCR group=1, non-pCR group=0

From these results, it is understood that it is possible to predict with a certain accuracy that a breast cancer patient will exhibit pCR as a result of a preoperative chemotherapy when a histogram prepared for the breast cancer patient based on the PID score of HER2 has the above-described pattern (B), particularly when the ratio of the cells having a PID score of 10 to 100 or so is high, or that the breast cancer patient will not exhibit pCR as a result of the preoperative chemotherapy when the histogram has the above-described pattern (A).

[Example 4] Analysis Utilizing Numerical Values Representing Expression Levels of HER1, HER2 and HER3 (Corresponding to First Embodiment of Present Invention)

From breast cancer tissues collected from breast cancer patients by needle biopsy for the purpose of prospective study at JBCRG (Japan Breast Cancer Research Group) in 2016, formalin-fixed paraffin-embedded tissue blocks (samples) were prepared in accordance with a conventional method, and these samples were each thin-sliced using a microtome to prepare specimen slides. Using the thus obtained specimen slides, DAB staining of the HER2 protein was performed using "HercepTest Kit" (manufactured by Dako Japan Co., Ltd.).

As a result of evaluating the DAB score, those patients diagnosed as HER2-positive were subjected to a preoperative chemotherapy of administering daunorubicin or doxorubicin, which is an anthracycline-based drug (topoisomerase inhibitor), for 3 months followed by administration of trastuzumab (trade name: Herceptin) and paclitaxel or docetaxel, which is a taxane-based drug (microtubule inhibitor), for 3 months. Thereafter, breast cancer tissue was removed by a surgery, and whether or not each patient exhibited pCR was assessed based on the presence or absence of observed invasion of cancer cells in the primary focus and metastasis of cancer cells to lymph nodes under a microscope.

Of 81 breast cancer patients who received the above-described preoperative chemotherapy, 48 patients exhibited pCR (pCR group) and 33 patients did not exhibit pCR (non-pCR group). Using specimen slides prepared from the samples (formalin-fixed paraffin-embedded tissue blocks) of these breast cancer patients that were collected and preserved prior to the preoperative chemotherapy, PID staining was performed for each of HER2, HER1 and HER3 to acquire PID scores in accordance with the below-described procedures (see Tables 1-1, 1-2, 1-3 and 1-4).

TABLE 1-1

| No. | JBCRG Case Reg. Number | Pathological judgment of preoperative chemotherapy | The number of PID particles per unit area of tissue after staining of HER2 | The number of PID particles per cell of tissue after staining of HER2 | The number of PID particles per cell of tissue after staining of HER1 | The number of PID particles per cell of tissue after staining of HER3 |
|---|---|---|---|---|---|---|
| 1 | 001 | non-pCR | 20.8 | 14.9 | 8.2 | 8.0 |
| 2 | 002 | non-PCR | 58.2 | 61.7 | 12.9 | 17.3 |
| 3 | 003 | pCR | 214.9 | 209.5 | 11.3 | 9.3 |
| 4 | 004 | pCR | 70.5 | 95.1 | 360.4 | 25.9 |
| 5 | 007 | non-pCR | 187.3 | 215.6 | 14.8 | 17.6 |
| 6 | 008 | pCR | 349.6 | 351.3 | 56.4 | 18.0 |
| 7 | 012 | pCR | 215.1 | 226.8 | 19.6 | 10.9 |
| 8 | 015 | non-pCR | 34.5 | 37.7 | 19.0 | 13.5 |
| 9 | 016 | pCR | 50.7 | 69.9 | 15.6 | 17.8 |
| 10 | 019 | non-pCR | 92.8 | 80.4 | 6.6 | 17.6 |
| 11 | 020 | pCR | 354.8 | 318.3 | 5.6 | 53.6 |
| 12 | 021 | pCR | 49.7 | 64.0 | 33.4 | 36.2 |
| 13 | 022 | pCR | 72.3 | 113.8 | 11.0 | 21.0 |
| 14 | 027 | non-pCR | 13.7 | 12.9 | 30.1 | 21.6 |
| 15 | 028 | pCR | 84.1 | 105.7 | 18.4 | 11.0 |
| 16 | 035 | non-pCR | 332.7 | 326.4 | 19.4 | 49.6 |
| 17 | 036 | non-pCR | 82.3 | 72.1 | 6.5 | 34.7 |
| 18 | 039 | non-pCR | 16.4 | 27.8 | 53.5 | 31.7 |
| 19 | 046 | non-pCR | 67.0 | 97.2 | 12.7 | 11.0 |
| 20 | 049 | non-pCR | 15.9 | 17.3 | 13.6 | 25.4 |

TABLE 1-2

| No. | JBCRG Case Reg. Number | Pathological judgment of preoperative chemotherapy | The number of PID particles per unit area of tissue after staining of HER2 | The number of PID particles per cell of tissue after staining of HER2 | The number of PID particles per cell of tissue after staining of HER1 | The number of PID particles per cell of tissue after staining of HER3 |
|---|---|---|---|---|---|---|
| 21 | 054 | pCR | 146.1 | 116.4 | 7.6 | 13.0 |
| 22 | 055 | pCR | 225.7 | 216.8 | 36.4 | 14.6 |
| 23 | 058 | non-pCR | 9.5 | 6.3 | 11.3 | 8.1 |
| 24 | 066 | non-pCR | 218.6 | 173.4 | 22.3 | 16.7 |
| 25 | 069 | non-pCR | 157.0 | 196.2 | 13.7 | 33.8 |
| 26 | 070 | non-pCR | 8.4 | 8.5 | 6.6 | 136 |
| 27 | 073 | non-pCR | 100.9 | 74.9 | 10.0 | 13.2 |
| 28 | 074 | pCR | 163.8 | 203.9 | 12.1 | 16.2 |
| 29 | 082 | pCR | 214.1 | 212.5 | 9.9 | 16.6 |

TABLE 1-2-continued

| No. | JBCRG Case Reg. Number | Pathological judgment of preoperative chemotherapy | The number of PID particles per unit area of tissue after staining of HER2 | The number of PID particles per cell of tissue after staining of HER2 | The number of PID particles per cell of tissue after staining of HER1 | The number of PID particles per cell of tissue after staining of HER3 |
|---|---|---|---|---|---|---|
| 30 | 083 | non-pCR | 37.8 | 31.0 | 7.8 | 90.4 |
| 31 | 085 | pCR | 300.3 | 429.7 | 24.7 | 17.9 |
| 32 | 088 | pCR | 414.6 | 551.2 | 20.5 | 15.1 |
| 33 | 092 | pCR | 29.8 | 25.4 | 16.6 | 11.6 |
| 34 | 096 | pCR | 288.5 | 336.6 | 11.7 | 19.2 |
| 35 | 098 | pCR | 51.2 | 75.1 | 15.2 | 12.3 |
| 36 | 099 | pCR | 108.2 | 146.1 | 17.2 | 25.4 |
| 37 | 102 | pCR | 226.5 | 215.2 | 12.4 | 33.3 |
| 38 | 107 | non-pCR | 191.0 | 286.3 | 23.4 | 54.2 |
| 39 | 108 | pCR | 127.6 | 150.3 | 7.0 | 12.3 |
| 40 | 109 | pCR | 88.3 | 127.4 | 93.7 | 71.6 |
| 41 | 110 | pCR | 202.2 | 279.8 | 7.7 | 66.7 |
| 42 | 112 | pCR | 169.3 | 219.6 | 4.6 | 22.9 |

TABLE 1-3

| No. | JBCRG Case Reg. Number | Pathological judgment of preoperative chemotherapy | The number of PID particles per unit area of tissue after staining of HER2 | The number of PID particles per cell of tissue after staining of HER2 | The number of PID particles per cell of tissue after staining of HER1 | The number of PID particles per cell of tissue after staining of HER3 |
|---|---|---|---|---|---|---|
| 43 | 115 | pCR | 117.5 | 133.9 | 12.3 | 13.3 |
| 44 | 118 | non-pCR | 112.3 | 138.4 | 18.9 | 32.4 |
| 45 | 120 | pCR | 371.5 | 488.7 | 17.5 | 11.2 |
| 46 | 126 | pCR | 45.7 | 42.1 | 15.7 | 11.4 |
| 47 | 130 | pCR | 210.9 | 221.8 | 10.7 | 17.1 |
| 48 | 132 | non-pCR | 54.4 | 57.0 | 14.5 | 43.6 |
| 49 | 133 | pCR | 211.3 | 279.2 | 4.8 | 19.3 |
| 50 | 135 | non-pCR | 94.2 | 111.7 | 13.9 | 33.0 |
| 51 | 138 | pCR | 86.2 | 68.5 | 13.2 | 29.3 |
| 52 | 140 | non-pCR | 181.0 | 164.8 | 8.4 | 18.6 |
| 53 | 141 | pCR | 260.9 | 199.9 | 8.3 | 17.1 |
| 54 | 143 | pCR | 228.5 | 349.8 | 9.8 | 32.2 |
| 55 | 147 | pCR | 157.4 | 177.8 | 4.9 | 12.8 |
| 56 | 148 | pCR | 173.3 | 307.6 | 7.0 | 17.8 |
| 57 | 151 | non-pCR | 156.9 | 188.1 | 8.6 | 10.2 |
| 58 | 152 | pCR | 141.5 | 158.7 | 14.6 | 15.2 |
| 59 | 155 | pCR | 195.4 | 234.0 | 11.4 | 16.1 |
| 60 | 156 | pCR | 64.2 | 73.6 | 5.3 | 14.9 |
| 61 | 161 | non-pCR | 94.5 | 95.3 | 5.3 | 13.3 |
| 62 | 162 | pCR | 199.2 | 192.9 | 7.8 | 18.3 |
| 63 | 164 | pCR | 288.3 | 399.1 | 14.0 | 33.1 |
| 64 | 165 | pCR | 113.5 | 157.3 | 13.4 | 43.6 |

TABLE 1-4

| No. | JBCRG Case Reg. Number | Pathological judgment of preoperative chemotherapy | The number of PID particles per unit area of tissue after staining of HER2 | The number of PID particles per cell of tissue after staining of HER2 | The number of PID particles per cell of tissue after staining of HER1 | The number of PID particles per cell of tissue after staining of HER3 |
|---|---|---|---|---|---|---|
| 65 | 167 | pCR | 232.0 | 247.1 | 9.2 | 19.1 |
| 66 | 173 | non-pCR | 5.5 | 9.3 | 14.0 | 19.9 |
| 67 | 176 | pCR | 158.9 | 181.7 | 7.8 | 20.0 |
| 68 | 179 | non-pCR | 98.1 | 112.4 | 13.0 | 46.6 |
| 69 | 180 | non-pCR | 10.4 | 10.7 | 5.9 | 16.8 |
| 70 | 181 | non-pCR | 8.0 | 7.9 | 3.7 | 32.9 |
| 71 | 182 | non-pCR | 8.7 | 19.0 | 22.8 | 18.4 |
| 72 | 183 | non-pCR | 65.1 | 48.0 | 8.3 | 145.2 |
| 73 | 184 | non-pCR | 98.4 | 128.8 | 8.3 | 19.6 |
| 74 | 189 | pCR | 44.6 | 49.9 | 4.2 | 35.2 |
| 75 | 191 | pCR | 92.7 | 98.4 | 4.8 | 12.4 |
| 76 | 194 | non-pCR | 198.1 | 347.6 | 34.0 | 66.1 |
| 77 | 197 | pCR | 121.0 | 200.7 | 24.1 | 26.5 |
| 78 | 208 | non-pCR | 85.7 | 71.7 | 24.8 | 22.6 |
| 79 | 211 | pCR | 12.5 | 11.2 | 8.9 | 12.4 |
| 80 | 213 | pCR | 153.2 | 182.8 | 7.1 | 27.3 |
| 81 | 215 | pCR | 292.5 | 458.0 | 13.7 | 47.8 |

In addition, using the specimen slides prepared from the above-described samples, DAB staining of HER2 protein and FISH of the HER2 gene were also performed in parallel with the acquisition of PID scores in the same manner as in Example 1.

(4-1) PID Staining of HER2 and Acquisition of PID Score

PID Staining of HER2 as well as a staining treatment for morphological observation and the specimen post-treatment step were performed in the same manner as in Example 1, except that the streptavidin-modified perylene diimide-integrated melamine resin particles prepared in Preparation Example 3 were used in the fluorescent labeling treatment of immunostaining in place of the streptavidin-modified Texas Red-integrated melamine resin particles.

(4-2) Evaluation Step

The observation and image-capturing step as well as image processing were performed in the same manner as in Example 1, and the bright spots representing the perylene diimide dye-integrated melamine resin particles labeling the HER2 proteins expressed on the cell membranes were extracted and counted as the number of PID particles. Among the bright spots on the cell membranes, ones having a brightness of not less than a prescribed value were converted into the number of PID particles by dividing the brightness of such bright spots by the brightness per each of the perylene diimide dye-integrated melamine resin particles. The number of the bright spots of HER2 was measured in five visual fields for each stained slide.

The average number of PID particles per unit area (100 μm²) or the average number of PID particles per each of 100 cells selected in each of the five visual fields on each stained slide was measured (this process corresponds to the "index acquisition step" in the test support method of the present invention).

(4-3) PID Staining of HER1 and Acquisition of PID Score

PID staining of HER1 and acquisition of PID scores were performed in the same manner as in the above-described step (1-2).

(4-4) PID Staining of HER3 and Acquisition of PID Score

PID staining of HER3 and acquisition of PID scores were performed in the same manner as in the above-described step (1-3).

(4-5) Analysis Results (4-5-1) Relationship of IHC-DAB Color Intensity and FISH Score with pCR FIG. 13 shows the color intensity per unit tissue area (100 μm²) obtained by the IHC-DAB staining for the pCR group and the non-pCR group. FIG. 14 shows the FISH score for the pCR group and the non-pCR group.

Both of these figures were obtained for HER2. In Mann-Whitney U test, no significant difference was found between the pCR group and the non-pCR group in terms of both the DAB color intensity and the FISH score (p>0.05 for both of these items).

(4-5-2) Relationship Between PID Score of HER2 and pCR

FIGS. 15 and 16 show the PID scores of HER2 protein for the pCR group and the non-pCR group (FIG. 15 shows the average number of PID particles per unit tissue area (100 μm²) as a PID score, and FIG. 16 shows the average number of PID particles per cell as a PID score). In Mann-Whitney U test, a significant difference was found between the pCR group and the non-pCR group in terms of the PID score (p<0.05). Here, it was confirmed that equivalent p-values were obtained for all of the PID values. The PID scores calculated hereinbelow are average values of the number of PID particles per cell.

FIG. 17 shows an ROC curve (receiver operating characteristic curve) for the PID score, which was prepared based on the above-described results. The preset optimum cut-off value was 54.1 and, in this case, the sensitivity (ordinate) was 71% and the specificity (abscissa) was 60%, meaning that the false-positive rate (1−specificity) was 40%.

From these results, it is understood that, although whether or not pCR will be attained cannot be predicted prior to a preoperative chemotherapy using the IHC-DAB color intensity and the FISH score, the use of the PID score for HER2 protein enables to make the prediction with certain accuracy even if the results are provided only for HER2.

(4-5-3) Relationship of PID Score of HER1 and PID Score Ratio of HER2/HER1 with PCR FIG. 18 provides a box plot showing the PID scores of HER1 protein that were obtained in the above-described (4-2) for the pCR group and the non-pCR group.

From the PID scores of HER2 protein that were obtained in the above-described (4-1) and the PID scores of HER1 protein that were obtained in the above-described (4-2), the ratio thereof (PID score of HER2/PID score of HER1) was calculated and compared between the pCR group and the non-pCR group.

FIG. 19 provides a box plot showing the PID score ratio of HER2/HER1, which was prepared based on the above-described results. In Mann-Whitney U test, a significant difference was found between the pCR group and the non-pCR group (p<0.001, Mann-Whitney U test).

From these results, it is believed that whether or not pCR will be attained can be predicted more accurately by using the PID score ratio of HER2/HER1 (p<0.001) as an index than using the PID score of HER2 alone (p<0.05) as an index.

(4-5-4) Relationship of PID Score of HER3 and PID Score Ratio of HER2/HER3 with pCR FIG. 20 provides a box plot showing the PID scores of HER3 protein that were obtained in the above-described (4-3) for the pCR group and the non-pCR group.

From the PID scores of HER2 protein that were obtained in the above-described (4-1) and the PID scores of HER3 protein that were obtained in the above-described (1-3), the ratios thereof (PID score of HER2/PID score of HER3 and PID score of HER3/PID score of HER2) were calculated and compared between the pCR group and the non-pCR group.

FIG. 21 provides a box plot showing the PID score ratio of HER2/HER3, which was prepared based on the above-described results. In Mann-Whitney U test, a significant difference was found between the pCR group and the non-pCR group (p<0.001).

From these results, it is believed that whether or not pCR will be attained can be predicted more accurately by using the PID score ratio of HER2/HER3 (p<0.001) as an index than using the PID score of HER2 alone (p<0.05) as an index.

FIG. 22 provides a box plot showing the PID score ratio of HER3/HER2, which was prepared based on the above-described results. In Mann-Whitney U test, a significant difference was found between the pCR group and the non-pCR group (p<0.001).

From these results, it is believed that whether or not pCR will be attained can be predicted more accurately by using the PID score ratio of HER3/HER2 (p<0.001) as an index than using the PID score of HER2 alone (p<0.05) as an index.

[Example 5] Analysis Utilizing Distribution Pattern of Histogram Prepared Based on Expression Level of HER2 Per Cell (Corresponding to Second Embodiment of Present Invention)

Among those samples collected from breast cancer tissues of breast cancer patients by needle biopsy at JBCRG during the period of 2011 to 2014, for 81 samples having a sufficient amount, the PID score of HER2 protein (number of PID bright spots per unit area) was obtained in the same manner as in the above-described (4-1) of Example 1. Based on the results thereof, histograms showing the PID score on the abscissa (a total of 41 classes each having a width of 10 PIDs) and the number of cells on the ordinate (a total number of cells in 5 visual fields on a single stained slide) were prepared. Not all of the thus prepared histograms are shown here, and only the results obtained by patterning and tabulating the histograms are provided (see Table 2).

TABLE 2

| | pCR | Non-pCR |
|---|---|---|
| (A) Pattern having a peak at the number of bright spots = 0 | 10 | 21 |
| (B) Unimodal pattern in which the peak is shifted to the right | 27 | 8 |
| (C) Bimodal or multimodal pattern | 7 | 3 |
| (D) Pattern distributed over a wide range of classes | 4 | 1 |

From these results, it is understood that it is possible to predict with a certain accuracy that a breast cancer patient will exhibit pCR as a result of a preoperative chemotherapy when a histogram prepared for the breast cancer patient based on the PID score of HER2 has the above-described pattern (B), particularly when the ratio of the cells having a PID score of 10 to 100 or so is high, or that the breast cancer patient will not exhibit pCR as a result of the preoperative chemotherapy when the histogram has the above-described pattern (A).

[Example 6] Analysis Utilizing Specimen Slides Prepared from Tissues Collected from Model Animals PID staining of the HER2 protein was performed, the number of bright spots derived from HER2 was measured, and the PID score was obtained in the same manner as in Example 1, except that specimen slides prepared using tissues collected from PDX mice (patient-derived xenograft mice) were used as tissue specimens to be tested.

PDX is an abbreviation for "patient-derived tumor xenograft", and a PDX animal is an animal prepared by transplanting a patient (human)-derived tumor tissue into a mouse or other experimental animal and allowing the tumor tissue to grow in the body of the mouse or the like for a certain period. Transplantation of such a human-derived tumor tissue grown in the body of a mouse to another mouse is referred to as "subculture", and it is also possible to allow a tumor tissue collected from a patient to be succeeded over generations by subculture. In recent years, discussions have been made on the benefits of utilizing such a mouse transplanted with a tumor tissue of a patient or a mouse subcultured with the tumor tissue of the transplanted mouse, instead of using a tumor collected from the patient as a sample.

The tissue specimens used in this Example were prepared by the following procedures.

(1) Sample acquisition: Breast cancer patient samples of 1 $cm^3$ in size to be transplanted were purchased from a clinical sample supplier, Sofia Bio LLC.

(2) Preparation of PDX mice: Tumor tissues collected from 8 breast cancer patients who had received a preoperative chemotherapy (5 patients exhibited pCR (pCR group) and 3 patients did not exhibit pCR (non-pCR group)) were each subcutaneously transplanted at a size of 3 $mm^3$ into three severe combined immunodeficiency mice (NOD-SCID mice). The mice were kept in a sterile facility for about a month, and the tumor tissues were collected once they grew to a size of 1 $cm^3$. The thus collected tumor tissues were each fixed with 10% formalin for 24 hours, and paraffin-embedded tissue blocks were subsequently prepared therefrom in accordance with a conventional method and stored.

(3) Staining of Paraffin Section Slides

The thus obtained paraffin blocks were each cut out at a thickness of 4 μm and pasted onto a glass slide to prepare specimen slides. Then, DAB staining and PID staining were performed on HER2 protein and evaluated in the same manner as in Example 1. As a result, the same tread as observed in Example 1 was obtained.

[Reference Example] Evaluation of Binding Force Between Single Streptavidin-Modified PID Particle and Biotin of Specific Density The amount of binding between biotin immobilized on a gold substrate at a certain density and PID particles was measured using an AFM (FIG. 25A). An AFM cantilever was coated with streptavidin-modified PID particles via PEG chains (FIGS. 25A and 25B). In order to allow biotin on the gold substrate to have a prescribed density, biotinylated PEG alkanethiol as biotin-conjugated molecules and (11-mercaptoundecyl)triethylene glycol as spacer molecules were mixed at a ratio of 0:10 (condition I) or 3:7 (condition II) in terms of the number of molecules. When the thus obtained mixture was added onto the gold substrate, a self-assembled film of these molecules was formed on the gold substrate due to the affinity of the thiol groups for gold. From each binding force-distance curve obtained by AFM measurement for the streptavidin-modified PID particles and the molecules immobilized on the substrate, a histogram showing the distribution of the binding force between these molecules was prepared, and the average binding force was calculated. According to the results thereof, the average binding force in the condition I is 95.7 pN (FIG. 25C), and it is believed that this binding force is primarily attributed to non-specific interactions acting between PID-modifying streptavidin and ethylene glycol of the spacer molecules, such as van der Walls force. Meanwhile, the average binding force in the condition II is 135.5 pN (FIG. 25D), and the binding force is thus different by about 40 pN between the conditions I and II. This difference is the same as the binding force between a single streptavidin molecule and a single biotin molecule that has been reported on many occasions; therefore, it is suggested that 1:1-binding of streptavidin and biotin was successfully detected under the condition II of the experiment shown in Reference Example. Further, when the binding force was measured under the condition II after blocking streptavidin with a blocking reagent (condition III), the average binding force was reduced to 94.0 pN (FIG. 25E). This value is the same as the value of the condition I and thus indicates that the binding between biotin on the gold substrate surface and streptavidin on the PID surface was inhibited by the blocking.

The entire disclosures of Japanese patent Application No. 2016-220490, filed on Nov. 11, 2016, and Application No. 2017-111031, filed on Jun. 5, 2017, are incorporated herein by reference in its entirety.

What is claimed is:

1. A test support method for supporting the prediction of pathological complete response (pCR) to preoperative therapy in a breast cancer patient by using a breast cancer tissue section collected from the breast cancer patient, the test support method comprising the following steps [1], [2], and [3]:

Step [1]: A step of acquiring a fluorescence image of the breast cancer tissue section, wherein the fluorescence image shows bright spots of fluorescent nanoparticles labeling two or more kinds of breast cancer-related proteins including at least HER2;

Step [2]: A step of acquiring, on the basis of the bright spots of the fluorescence image, a plurality of indexes, wherein numerical value(s) representing the expression level(s) of the breast cancer-related protein(s) are acquired as a first of the indexes, a histogram based on the expression level(s) per cell is prepared as a second of the indexes, and a ratio of HER2 expression level/an expression level of a breast cancer protein other than HER2 is calculated as a third of the indexes; and Step [3]: A step of acquiring information for predicting pCR by performing an analysis which comprises a combination of (a) comparing the numerical value(s) with prescribed threshold value(s), (b) classifying the distribution pattern of the histogram into one of four distribution patterns: (A) a distribution pattern having a peak at the number of the bright spots=0; (B) a unimodal distribution pattern in which the peak is shifted to a right; (C) a bimodal or multimodal distribution pattern; and (D) a distribution pattern with distribution over a wide range of classes, and (c) comparing the ratio with a prescribed threshold value.

2. The test support method according to claim 1, wherein The step [2] comprises acquiring, on the basis of the bright spots of the fluorescence image, numerical values representing the expression levels of each of the two or more kinds of breast cancer-related proteins as the first of the indexes.

3. The test support method according to claim 2, wherein The step [1] comprises acquiring a fluorescence image of the breast cancer tissue section, which fluorescence image shows bright spots of fluorescent nanoparticles labeling HER2 and HER1, or HER2 and HER3, The step [2] comprises acquiring numerical values representing the expression levels of each of HER2 and HER1, or HER2 and HER3 on the basis of the bright spots of the fluorescence image and calculating, as the third of the indexes, a ratio (a) of the expression level of HER2/the expression level of HER1 or a ratio (b) of the expression level of HER2/the expression level of HER3, and The step [3] comprises acquiring information for predicting pCR by performing an analysis which comprises comparing the ratio (a) or (b) with a prescribed threshold value.

4. The test support method according to claim 1, wherein the analysis comprises (a) comparing the numerical value representing the expression level of HER2 with the prescribed threshold value and (b) classifying the distribution pattern of the histogram based on the expression level of HER2 per cell.

5. The test support method according to claim 2, wherein, in the step [1], the two or more kinds of breast cancer-related proteins including at least HER2 are labeled on a single breast cancer tissue section with two or more colors of fluorescent nanoparticles that correspond to the respective proteins.

6. The test support method according to claim 3, wherein, in the step [1], the two or more kinds of breast cancer-related proteins including at least HER2 are labeled on a single breast cancer tissue section with two or more colors of fluorescent nanoparticles that correspond to the respective proteins.

7. The test support method according to claim 4, wherein, in the step [1], the breast cancer-related proteins including at least HER2 are labeled on a single breast cancer tissue section with two or more colors of fluorescent nanoparticles that correspond to the respective proteins.

* * * * *